US006537554B1

(12) United States Patent
Shimkets et al.

(10) Patent No.: US 6,537,554 B1
(45) Date of Patent: Mar. 25, 2003

(54) NUCLEOTIDE SEQUENCES AND AMINO ACID SEQUENCES OF SECRETED PROTEINS INVOLVED IN ANGIOGENESIS

(75) Inventors: Richard A. Shimkets, West Haven, CT (US); Michael Jeffers, Branford, CT (US)

(73) Assignee: Curagen Corporation, New Haven, CT (US)

( * ) Notice: Subject to any disclaimer, the term of this patent is extended or adjusted under 35 U.S.C. 154(b) by 64 days.

(21) Appl. No.: 09/658,644

(22) Filed: Sep. 11, 2000

Related U.S. Application Data

(63) Continuation-in-part of application No. 09/150,684, filed on Sep. 10, 1998.

(51) Int. Cl.[7] .................... A61K 39/00; A61K 39/38; C12Q 1/00; G01N 33/48
(52) U.S. Cl. ............... 424/198.1; 424/184.1; 435/4; 436/64
(58) Field of Search .................. 436/64; 424/184.1, 424/198.1; 435/4

(56) References Cited

U.S. PATENT DOCUMENTS

| 4,518,584 A | 5/1985 | Mark et al. |
|---|---|---|
| 5,382,514 A | 1/1995 | Passaniti et al. |
| 5,434,185 A | 7/1995 | Collins et al. |
| 5,563,130 A | 10/1996 | Backer et al. |
| 5,567,693 A | 10/1996 | Backer et al. |
| 5,574,026 A | 11/1996 | Backer et al. |
| 5,593,990 A | 1/1997 | D'Amato |
| 5,610,166 A | 3/1997 | Singh |
| 5,629,327 A | 5/1997 | D'Amato |
| 5,629,340 A | 5/1997 | Kuwano et al. |
| 5,639,725 A | 6/1997 | O'Reilly et al. |
| 5,646,136 A | 7/1997 | Petrow et al. |
| 5,698,586 A | 12/1997 | Kishimoto et al. |
| 5,712,291 A | 1/1998 | D'Amato |
| 5,721,226 A | 2/1998 | Frye et al. |
| 5,733,876 A | 3/1998 | O'Reilly et al. |
| 5,744,492 A | 4/1998 | Kohn et al. |
| 5,753,230 A | 5/1998 | Brooks et al. |
| 5,766,591 A | 6/1998 | Brooks et al. |

FOREIGN PATENT DOCUMENTS

| WO | WO98/16644 | 4/1998 |
|---|---|---|
| WO | WO99/15653 | 4/1999 |
| WO | WO99/40193 | 8/1999 |

OTHER PUBLICATIONS

Battegay, 1995. "Angiogenesis: mechanistic insights, neovascular diseases, and therapeutic prospects." J Mol Med. 73: 333–46.

Chen, et al., 1994. "Correlation between angiogenesis and basic fibroblast growth factor expression in experimental brain infarct." Stroke. 25: 1651–1657.

Couffinhal, et al., 1998. "Mouse model of angiogenesis." Am J Pathol. 152: 1667–1679.

Christersson, et al. 1992. "Topical application of tetracycline–HCl in human periodontitis." J. Clin. Periodontol 20:88–95.

Folkman, et al., 1992. "Angiogenesis." J Biol Chem. 267: 10931–10934.

Harada, et al., 1994. "Basic fibroblast growth factor improves myocardial function in chronically ischemic porcine hearts." J Clin Invest. 94: 623–630.

Koblizek, et al., 1998. "Angiopoietin–1 induces sprouting angiogenesis in vitro." Curr Biol. 8: 529–532.

Krstenansky, et al., 1987. "Antithrombin properties of C–terminus of hirudin using synthetic unsulfated N alpha–acetyl–hirudin45–65." FEBS Lett. 211: 10–16.

Maisonpierre, et al., 1997. "Angiopoietin–2, a natural antagonist for Tie2 that disrupts in vivo angiogenesis." Science. 277: 55–60.

McDowell and Gadek. 1992. "Structural studies of potent constrained RGD peptides." J. Am Chem. Soc. 114:9245–9253.

Merrifield. 1963. "Solid phase peptide synthesis. I. The synthesis of a tetrapeptide." J. Am. Chem. Soc. 85:2149–2154.

Pu, et al., 1993. "Enhanced revascularization of the ischemic limb by angiogenic therapy." Circulation. 88: 208–215.

Suri, et al., 1996. "Requisite role of angiopoietin–1, a ligand for the TIE2 receptor, during embryonic angiogenesis." Cell. 87: 1171–1180.

Takeshita, et al., 1994. "Therapeutic angiogenesis. A single intraarterial bolus of vascular endothelial growth factor augments revascularization in a rabbit ischemic hind limb model." J Clin Invest. 93: 662–670.

Yanagisawa–Miwa, et al., 1992. "Salvage of infarcted myocardium by angiogenic action of basic fibroblast growth factor." Science. 257: 1401–1403.

Zetter, 1998. "Angiogenesis and tumor metastasis." Ann Rev Med. 49: 407–427.

Bicknell, 1994. "Vascular targeting and the inhibition of angiogenesis." Ann. Oncol. 5 (suppl.) 4: 45–50.

Dameron, et al., 1994. "Control of angiogenesis in fibroblasts by p53 regulatin of thrombospondin–1." Science 265: 1582–1584.

Davis, et al., 1996. "Isolation of angiopoietin–1, a ligand for the TIE2 receptor, by secretion–trap expression cloning." Cell 87: 1161–1169.

(List continued on next page.)

Primary Examiner—Anthony C. Caputa
Assistant Examiner—Gary B. Nickol
(74) Attorney, Agent, or Firm—Mintz, Levin; Ivor R. Elrifi; Naomi S. Biswas

(57) ABSTRACT

Novel angiogenesis/anti-angiogenesis secreted proteins and the nucleic acid sequences which encode them are disclosed by the present invention.

4 Claims, 9 Drawing Sheets

OTHER PUBLICATIONS

Fernig, et al., 1994. "Fibroblast growth factors and their receptors: an information network controlling tissue growth, morphogenesis and repair." Prog. Growth Factor Res. 5: 353–377.

Kaufman, et al., 1991. "Improved vectors for stable expression of foreign genes in mammalian cells by use of the untranslated leader sequence from EMC virus." Nucleic Acids Res. 19: 4485–4490.

Kaufman, 1990. "Selection and coamplification of heterologous genes in mammalian cells." Methods Enzymol. 185:537–566.

Saragovi, et al., 1992. "Loops and secondary structure mimetics: development and applications in basic science and rational drug design." Bio/Technology 10: 773–778.

Vukicevic, et al., 1992. "Identification of multiple active growth factors in basement membrane Matrigel suggests caution in interpretation of cellular activity related to extracellular matrix components." Exp. Cell Res. 202: 1–8.

Beck and D'Amore, 1997. "Vascular development: cellular and molecular regulation." The FASEB Journal 11: 365–373.

Kim et al., 1999. "Molecular cloning and characterization of a novel angiopoietin family protein, angiopoietin-3." FEBS Letters 443: 353–356.

Ohbayashi et al., 1998. "Structure and Expression of the mRNA Encoding a Novel Fibroblast Growth Factor, FGF–18." Journal of Biological Chemistry 273: 18161–18154.

Proels et al., 1997. "Assignment of the microvascular endothelial differentiation gene 1 (MDG1) to human chromosome band 14q24.2 → q24.3 by fluorescence in situ hybridization." Cytogenet. Cell Genet. 79: 149–150.

Proels et al., 1997, rat Microvascular endothelial differentiation protein. Accession No. P97554 (XP–002133852).

Ye et al., 1999, MGD1 (*Homo sapiens*) protein, Accession No. AF083247 (XP–002133853).

Ye et al., 1999, MGD1 (*Homo sapiens*) protein, Accession No. AAD39845.

Hu et al., 1998, *Homo sapiens* fibroblast growth factor 18 (FGF18) mRNA, complete CDS, Accession No. AF075292.

Kim et al., 1999, *Homo sapiens* angiopoietin Y1 mRNA, complete CDS, Accession No. AF107253.

Hu, et al. (1998). "FGF–18, a novel member of the fibroblast growth factor family, stimulates hepatic and intestinal proliferation." Molecular and Cellular Biology 18(10): 6063–6074. Line Thru.

Gura, T. 1997. "Systems for identifying new drugs are often faulty." Science 278:1041–1042.

Lazar, E. et al. 1988. "Transforming growth factor α: Mutation of aspartic acid 47 and leucine 48 results in different biological activities." Mol. and Cell. Bio. 8:1247–1252.

Burgess, W. et al. 1990. "Possible dissociations of the Heparin–binding and mitogenic activities of Heparin–binding (Acidic fibroblast) growth factor–1 from it's receptor-binding activities by site–directed mutagenesis of a single lysine residue." J. Cell Bio. 111:2129–2138.

Bowie, J. et al. 1990. "Deciphering the message in protein sequences: Tolerance to amino acid substitutions." 247:1306–1310.

Bork, P. 2000. "Powers and pitfalls in sequence analysis: The 70% Hurdle." Genome Research 10:398–400.

Angiopoeitin-3

1
ATCTGGGTCAGCTGCAGCTGGTTACTGCATTTCTCCATGTGGCAGACAGAGCAAAGCCACAACGCTTTCTCTGCTGGATT

81
AAAGACGGCCCACAGACCAGAACTTCCACTATACTACTTAAAATTACATAGGTGGCTTGTCAAATTCAATTGATTAGTAT

161
TGTAAAAGGAAAAAGAAGTTCCTTCTTACAGCTTGGATTCAACGGTCCAAAACAAAAATGCAGCTGCCATTAAAGTCACA

241
GATGAACAAACTTCTACACTGATTTTTAAAATCAAGAATAAGGGCAGCAAGTTTCTGGATTCACTGAATCAACAGACACA

321
AAAAGACATCATTTTACAACCTCATTTCAAAATGAAGACTTTTACCTGGACCCTAGGTGTGCTATTCTTCCTACTAGTGG
```
                                                MetLysThrPheThrTrpThrLeuGlyValLeuPhePheLeuLeuValA
```

401
ACACTGGACATTGCAGAGGTGGACAATTCAAAATTAAAAAAATAAACCAGAGAAGATACCCTCGTGCCACAGATGGTAAA
```
spThrGlyHisCysArgGlyGlyGlnPheLysIleLysLysIleAsnGlnArgArgTyrProArgAlaThrAspGlyLys
```

481
GAGGAAGCAAAGAAATGTGCATACACATTCCTGGTACCTGACCAAAGAATAACAGGGCCAATCTGTGTCAACACCAAGGG
```
GluGluAlaLysLysCysAlaTyrThrPheLeuValProAspGlnArgIleThrGlyProIleCysValAsnThrLysGl
```

561
GCAAGATGCAAGTACCATTAAAGACATGATCACCAGGATGGACCTTGAAAACCTGAAGGATGTGCTCTCCAGGCAGAAGC
```
yGlnAspAlaSerThrIleLysAspMetIleThrArgMetAspLeuGluAsnLeuLysAspValLeuSerArgGlnLysA
```

641
GGGAGATAGATGTTCTGCAACTGGTGGTGGATGTAGATGGAAACATTGTGAATGAGGTAAAGCTGCTGAGAAAGGAAAGC
```
rgGluIleAspValLeuGlnLeuValValAspValAspGlyAsnIleValAsnGluValLysLeuLeuArgLysGluSer
```

721
CGTAACATGAACTCTCGTGTTACTCAACTCTATATGCAATTATTACATGAGATTATCCGTAAGAGGGATAATTCACTTGA
```
ArgAsnMetAsnSerArgValThrGlnLeuTyrMetGlnLeuLeuHisGluIleIleArgLysArgAspAsnSerLeuGl
```

801
ACTTTCCCAACTGGAAAACAAAATCCTCAATGTCACCACAGAAATGTTGAAGATGGCAACAAGATACAGGGAACTAGAGG
```
uLeuSerGlnLeuGluAsnLysIleLeuAsnValThrThrGluMetLeuLysMetAlaThrArgTyrArgGluLeuGluV
```

881
TGAAATACGCTTCCTTGACTGATCTTGTCAATAACCAATCTGTGATGATCACTTTGTTGGAAGAACAGTGCTTGAGGATA
```
alLysTyrAlaSerLeuThrAspLeuValAsnAsnGlnSerValMetIleThrLeuLeuGluGluGlnCysLeuArgIle
```

961
TTTTCCCGACAAGACACCCATGTGTCTCCCCCACTTGTCCAGGTGGTGCCACAACATATTCCTAACAGCCAACAGTATAC
```
PheSerArgGlnAspThrHisValSerProProLeuValGlnValValProGlnHisIleProAsnSerGlnGlnTyrTh
```

1041
TCCTGGTCTGCTGGGAGGTAACGAGATTCAGAGGGATCCAGGTTATCCCAGAGATTTAATGCCACCACCTGATCTGGCAA
```
rProGlyLeuLeuGlyGlyAsnGluIleGlnArgAspProGlyTyrProArgAspLeuMetProProProAspLeuAlaT
```

1121
CTTCTCCCACCAAAAGCCCTTTCAAGATACCACCGGTAACTTTCATCAATGAAGGACCATTCAAAGACTGTCAGCAAGCA
```
hrSerProThrLysSerProPheLysIleProProValThrPheIleAsnGluGlyProPheLysAspCysGlnGlnAla
```

Fig. 1

```
1201
     AAAGAAGCTGGGCATTCGGTCAGTGGGATTTATATGATTAAACCTGAAAACAGCAATGGACCAATGCAGTTATGGTGTGA
     LysGluAlaGlyHisSerValSerGlyIleTyrMetIleLysProGluAsnSerAsnGlyProMetGlnLeuTrpCysGl
1281
     AAACAGTTTGGACCCTGGGGGTTGGACTGTTATTCAGAAAAGAACAGACGGCTCTGTCAACTTCTTCAGAAATTGGGAAA
     uAsnSerLeuAspProGlyGlyTrpThrValIleGlnLysArgThrAspGlySerValAsnPhePheArgAsnTrpGluA
1361
     ATTATAAGAAAGGGTTTGGAAACATTGACGGAGAATACTGGCTTGGACTGGAAAATATCTATATGCTTAGCAATCAAGAT
     snTyrLysLysGlyPheGlyAsnIleAspGlyGluTyrTrpLeuGlyLeuGluAsnIleTyrMetLeuSerAsnGlnAsp
1441
     AATTACAAGTTATTGATTGAATTAGAAGACTGGAGTGATAAAAAAGTCTATGCAGAATACAGCAGCTTTCGTCTGGAACC
     AsnTyrLysLeuLeuIleGluLeuGluAspTrpSerAspLysLysValTyrAlaGluTyrSerSerPheArgLeuGluPr
1521
     TGAAAGTGAATTCTATAGACTGCGCCTGGGAACTTACCAGGGAAATGCAGGGGATTCTATGATGTGGCATAATGGTAAAC
     oGluSerGluPheTyrArgLeuArgLeuGlyThrTyrGlnGlyAsnAlaGlyAspSerMetMetTrpHisAsnGlyLysG
1601
     AATTCACCACACTGGACAGAGATAAAGATATGTATGCAGGAAACTGCGCCCACTTTCATAAAGGAGGCTGGTGGTACAAT
     lnPheThrThrLeuAspArgAspLysAspMetTyrAlaGlyAsnCysAlaHisPheHisLysGlyGlyTrpTrpTyrAsn
1681
     GCCTGTGCACATTCTAGCCTAAATGGAGTATGGTACAGAGGAGGCCATTACAGAAGCAAGCACCAAGATGGAATTTTCTG
     AlaCysAlaHisSerSerLeuAsnGlyValTrpTyrArgGlyGlyHisTyrArgSerLysHisGlnAspGlyIlePheTr
1761
     GGCCGAATACAGAGGCGGGTCATACTCCTTAAGAGCAGTTCAGATGATGATCAAGCCTATTGACTGAAGAGAGACACTCG
     pAlaGluTyrArgGlyGlySerTyrSerLeuArgAlaValGlnMetMetIleLysProIleAsp
1841
     CCAATTTAAATGACACAGAACTTTGTACTTTTCAGCTCTTAAAAATGTAAATGTTACATGTATATTACTTGGCACAATTT
1921
     ATTTCTACACATAAAGTTTTTAAAATGAATTTTACCGTAACTATAAAAGGGAACCTATAAATGTAGTTTCATCTGTCGTC
2001
     AATTACTGCAGAAAATTATGTGTATCCACAACCTAGTTATTTTAAAAATTATGTTGACTAAATACAAAGTTTGGTTTCTA
2081
     AAATGTAAATATTTGCCACAATGTAAAGCAAATCTTAGCTATATTTTAAATCATAAATAACATGTTCAAGATACTTAACA
2161
     ATTTATTTAAAATCTAAGATTGCTCTAACGTCTAGTGAAAAAAATATTTTTAAAATTTCAGCCAAATGATGCATTTTATT
2241
     TATAAAAATACAGACAGAAAATTAGGGAGAAACCTCTAGTTTTGCCAATAGAAAATGCTTCTTCCATTGAATAAAAGTTA
2321
     TTTCAAATCCAAAAAAAAAAAAAAAAAAAAAAAA
```

Fig. 1 (cont.)

hMEDG1

```
  1
     CGCCCGGGCAGTGCCCGGGGAAGGAGGAGCGCTAGGTCGGTGTACGACCGAGATTAGGGTGCGTGCCAGCTCCGGGAGGC
 81
     CGCGGTGAGGGGCCGGGCCCAAGCTGCCGACCCGAGCCGATCGTCAGGGTCGCCAGCGCCTCAGCTCTGTGGAGGAGCAG
161
     CAGTAGTCGGAGGGTGCAGGATATTAGAAATGGCTACTCCCCAGTCAATTTTCATCTTTGCAATCTGCATTTTAATGATA
                                     MetAlaThrProGlnSerIlePheIlePheAlaIleCysIleLeuMetIle
241
     ACAGAATTAATTCTGGCCTCAAAAAGCTACTATGATATCTTAGGTGTGCCAAAATCGGCATCAGAGCGCCAAATCAAGAA
     ThrGluLeuIleLeuAlaSerLysSerTyrTyrAspIleLeuGlyValProLysSerAlaSerGluArgGlnIleLysLy
321
     GGCCTTTCACAAGTTGGCCATGAAGTACCACCCTGACAAAAATAAGAGCCCGGATGCTGAAGCAAAATTCAGAGAGATTG
     sAlaPheHisLysLeuAlaMetLysTyrHisProAspLysAsnLysSerProAspAlaGluAlaLysPheArgGluIleA
401
     CAGAAGCATATGAAACACTCTCAGATGCTAATAGACGAAAAGAGTATGATACACTTGGACACAGTGCTTTTACTAGTGGT
     laGluAlaTyrGluThrLeuSerAspAlaAsnArgArgLysGluTyrAspThrLeuGlyHisSerAlaPheThrSerGly
481
     AAAGGACAAAGAGGTAGTGGAAGTTCTTTTGAGCAGTCATTTAACTTCAATTTTGATGACTTATTTAAAGACTTTGGCTT
     LysGlyGlnArgGlySerGlySerSerPheGluGlnSerPheAsnPheAsnPheAspAspLeuPheLysAspPheGlyPh
561
     TTTTGGTCAAAACCAAAACACTGGATCCAAGAAGCGTTTTGAAAATCATTTCCAGACACGCCAGGATGGTGGTTCCAGTA
     ePheGlyGlnAsnGlnAsnThrGlySerLysLysArgPheGluAsnHisPheGlnThrArgGlnAspGlyGlySerSerA
641
     GACAAAGGCATCATTTCCAAGAATTTTCTTTTGGAGGTGGATTATTTGATGACATGTTTGAAGATATGGAGAAAATGTTT
     rgGlnArgHisHisPheGlnGluPheSerPheGlyGlyGlyLeuPheAspAspMetPheGluAspMetGluLysMetPhe
721
     TCTTTTAGTGGTTTTGACTCTACCAATCAGCATACAGTACAGACTGAAAATAGATTTCATGGATCTAGCAAGCACTGCAG
     SerPheSerGlyPheAspSerThrAsnGlnHisThrValGlnThrGluAsnArgPheHisGlySerSerLysHisCysAr
801
     GACTGTCACTCAACGAAGAGGAAATATGGTTACTACATACACTGACTGTTCAGGACAGTAGTTCTTATTCTATTCTCACT
     gThrValThrGlnArgArgGlyAsnMetValThrThrTyrThrAspCysSerGlyGln
881
     AAATCCAACTGGTTGACTCTTCCTCATTATCTTTGATGCTAAACAATTTTCTGTGAACTATTTTGACAAGTGCATGATTT
961
     CACTTTAAACAATTTGATATAGCTATTAAATATATTTAAGGGTTTTTTTTTTTG
```

Fig. 2

FGF-8b

1
GGCTGGGCTAGGAGCCGCCGCCTCCCTCCCGCCCAGCGATGTATTCAGCGCCCTCCGCCTGCACTTGCCTGTGTTTACAC
                              MetTyrSerAlaProSerAlaCysThrCysLeuCysLeuHis
81
TTCCTGCTGCTGTGCTTCCAGGTACAGGTGCTGGTTGCCGAGGAGAACGTGGACTTCCGCATCCACGTGGAGAACCAGAC
PheLeuLeuLeuCysPheGlnValGlnValLeuValAlaGluGluAsnValAspPheArgIleHisValGluAsnGlnTh
161
GCGGGCTCGGGACGATGTGAGCCGTAAGCAGCTGCGGCTGTACCAGCTCTACAGCCGGACCAGTGGGAAACACATCCAGG
rArgAlaArgAspAspValSerArgLysGlnLeuArgLeuTyrGlnLeuTyrSerArgThrSerGlyLysHisIleGlnV
241
TCCTGGGCCGCAGGATCAGTGCCCGCGGCGAGGATGGGGACAAGTATGCCCAGCTCCTAGTGGAGACAGACACCTTCGGT
alLeuGlyArgArgIleSerAlaArgGlyGluAspGlyAspLysTyrAlaGlnLeuLeuValGluThrAspThrPheGly
321
AGTCAAGTCCGGATCAAGGGCAAGGAGACGGAATTCTACCTGTGCATGAACCGCAAAGGCAAGCTCGTGGGGAAGCCCGA
SerGlnValArgIleLysGlyLysGluThrGluPheTyrLeuCysMetAsnArgLysGlyLysLeuValGlyLysProAs
401
TGGCACCAGCAAGGAGTGTGTGTTCATCGAGAAGGTTCTGGAGAACAACTACACGGCCCTGATGTCGGCTAAGTACTCCG
pGlyThrSerLysGluCysValPheIleGluLysValLeuGluAsnAsnTyrThrAlaLeuMetSerAlaLysTyrSerG
481
GCTGGTACGTGGGCTTTACCAAGAAGGGGCGGCCGCGGAAGGGCCCCAAGACCCGGGAGAACCAGCAGGACGTGCATTTC
lyTrpTyrValGlyPheThrLysLysGlyArgProArgLysGlyProLysThrArgGluAsnGlnGlnAspValHisPhe
561
ATTGAAGCGCTACCCCAAGGGGCAACCCGGAGCTTTAGAAGCCCTTCAAGTACACGACNGTGACCAAGAAGTCCCGTCCG
IleGluAlaLeuProGlnGlyAlaThrArgSerPheArgSerProSerSerThrArg---
641
GATCCGGCCCACACACCCTGCCTAAGGGCAACCCGCCGCGGGGCCCCT

Fig. 3A

FGF-8b

1
GGCTGGGCTAGGAGCCGCCGCCTCCCTCCCGCCCAGCGATGTATTCAGCGCCCTCCGCCTGCACTTGCCTGTGTTTACAC
                                  MetTyrSerAlaProSerAlaCysThrCysLeuCysLeuHis

81
TTCCTGCTGCTGTGCTTCCAGGTACAGGTGCTGGTTGCCGAGGAGAACGTGGACTTCCGCATCCACGTGGAGAACCAGAC
PheLeuLeuLeuCysPheGlnValGlnValLeuValAlaGluGluAsnValAspPheArgIleHisValGluAsnGlnTh

161
GCGGGCTCGGGACGATGTGAGCCGTAAGCAGCTGCGGCTGTACCAGCTCTACAGCCGGACCAGTGGGAAACACATCCAGG
rArgAlaArgAspAspValSerArgLysGlnLeuArgLeuTyrGlnLeuTyrSerArgThrSerGlyLysHisIleGlnV

241
TCCTGGGCCGCAGGATCAGTGCCCGCGGCGAGGATGGGGACAAGTATGCCCAGCTCCTAGTGGAGACAGACACCTTCGGT
alLeuGlyArgArgIleSerAlaArgGlyGluAspGlyAspLysTyrAlaGlnLeuLeuValGluThrAspThrPheGly

321
AGTCAAGTCCGGATCAAGGGCAAGGAGACGGAATTCTACCTGTGCATGAACCGCAAAGGCAAGCTCGTGGGGAAGCCCGA
SerGlnValArgIleLysGlyLysGluThrGluPheTyrLeuCysMetAsnArgLysGlyLysLeuValGlyLysProAs

401
TGGCACCAGCAAGGAGTGTGTGTTCATCGAGAAGGTTCTGGAGAACAACTACACGGCCCTGATGTCGGCTAAGTACTCCG
pGlyThrSerLysGluCysValPheIleGluLysValLeuGluAsnAsnTyrThrAlaLeuMetSerAlaLysTyrSerG

481
GCTGGTACGTGGGCTTCACCAAGAAGGGGCGGCCGCGGAAGGGCCCCAAGACCCGGGAGAACCAGCAGGACGTGCATTTC
lyTrpTyrValGlyPheThrLysLysGlyArgProArgLysGlyProLysThrArgGluAsnGlnGlnAspValHisPhe

561
ATGAAGCGCTACCCCAAGGGGCAGCCGGAGCTTCAGAAGCCCTTCAAGTACACGACGGTGACCAAGAGGTCCCGTCGGAT
MetLysArgTyrProLysGlyGlnProGluLeuGlnLysProPheLysTyrThrThrValThrLysArgSerArgArgIl

641
CCGGCCCACACACCCTGCCTAGGCCACCCCGCCGCGGCCCCTCAGGTCGCCCTGGCCACACTCACACTCCCAGAAAACTG
eArgProThrHisProAla

721
CATCAGAGGAATATTTTTACATGAAAAATAAGGAAGAAGCTCTATTTTTGNACATTGNGTTTAAAAGAAGACAAAAACTG

801
AACCAAAACTCTTGGGGGGAGGGGTGATAAGGA

Fig. 3B

NUCLEOTIDE SEQUENCES AND AMINO ACID SEQUENCES OF SECRETED PROTEINS INVOLVED IN ANGIOGENESIS

RELATED APPLICATIONS

This application is a continuation-in-part and claims priority to U.S. Ser. No. 09/150,684, filed Sep. 10, 1998. The contents of this application are incorporated by reference in their entirety.

FIELD OF THE INVENTION

The invention relates generally to nucleic acids and polypeptides and more particularly to nucleic acids encoding polypeptides related to previously described angiogenesis-modulating polypeptides, and to the polypeptides encoded by these nucleic acids.

BACKGROUND OF THE INVENTION

Under normal physiological conditions, humans or animals undergo angiogenesis, i.e., generation of new blood vessels into a tissue or organ, only in restricted situations. During angiogenesis, endothelial cells react to stimulation with finely tuned signaling responses. The "endothelium" is a thin layer of flat epithelial cells that lines serous cavities, lymph vessels, and blood vessels. In normal physiological states such as embryonic growth and wound healing, neovascularization is controlled by a balance of stimulatory and inhibitory angiogenic factors. These controls may fail and result in formation of an extensive capillary network during the development of many diseases including ischemic heart disease, ischemic peripheral vascular disease, tumor growth and metastasis, reproduction, embryogenesis, wound healing, bone repair, rheumatoid arthritis, diabetic retinopathy and other diseases.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The balance of positive or negative angiogenesis regulators control the fate of vascular wall cells. They remain either in a state of vascular homeostasis, or they proceed to neovascularization, e.g., tumor growth and the switch to an angiogenic tumor phenotype correlates with increased secretion of angiogenic molecules such as fibroblast growth factor (FGF), vascular endothelial growth factor (VEGF), and others. On the other hand, tumors also acquire a more angiogenic phenotype because inhibitors of angiogenesis are down-regulated during tumorigenesis (e.g. thrombospondin) (Dameron et al., 1994, Science 265:1582–1584).

Angiogenic and antiangiogenic (or angiostatic) molecules control the formation of new vessels via different mechanisms. Antiangiogenic molecules, or angiogenesis inhibitors (e.g. angiostatin, angiopoeitin-1 (Ang11), rat microvascular endothelial differentiation gene (MEDG), somatostatin, thrombospondin, platelet factor 4) can repress angiogenesis, and therefore, maintain vascular homeostasis (see, e.g. for review Bicknell, 1994, Ann. Oncol. 5 (suppl) 4:45–50).

Angiogenic molecules are capable of inducing the formation of new vessels and include, for example, but not for limitation, fibroblast growth factor (FGF), angiopoeitin 2 (Ang-2), erythroipoietin, hepatocyte growth factor (HGF), vascular endothelial growth factor (VEGF) and others (for review, see e.g. Folkman & Shing, 1992, J. Biol. Chem. 267:10931–10934). FGF elicit its effects mainly via direct action on relevant endothelial cells via its endothelial receptor (e.g. Folkman & Shing, 1992, J. Biol. Chem. 267:10931–10934). FGF lacks a signal sequence for secretion.

Angiogenesis has been implicated in ischemic heart and ischemic vascular disease. In myocardial infarction new vessels penetrate the necrotic area and the surrounding schemic tissue. Neovascularizations, together with inflammatory cells, remove cellular debris and play a role in tissue repair and remodeling that results in myocardial scar formation. FGF-induced mycoardial infarction and neovascularization (e.g. Yanagisawa-Miwa et al., 1992, Science 257:1401–1403; Harada et al., 1994, J. Clin. Invest. 94:623–630) show that angiogenesis contributes to the preservation of ischemic tissue and myocardial pump function in myocardial necrosis. This suggests a therapeutic use of angiogenic factors in clinical situations. Additional studies with FGF (Pu et al., 1993, Circulation 88:208–215) and VEGF (Takeshita et al., 1994, J. Clin. Invest 93:662–670) in peripheral ischemic vascular disease protected ischemic limbs. Similar to myocardial infarction, brain infarcts (strokes) are associated with angiogenesis (Chen et al., 1994, Stroke 25-1651–1657).

Likewise, angiogenesis has been implicated in various cancers. Angiogenesis is an essential component of the metastatic pathway (see, e.g. Zetter, 1998, Ann. Rev. Med. 49:407–427). These blood vessels provide the principal pathway by which tumor cells exit the primary tumor site and enter the circulation. Tumor angiogenesis is regulated by the production of angiogenic stimulators including members of the FGF and VEGF families (see, e.g. Fernig & Gallaher, 1994, Prog. Growth Factor Res. 5:353–377). Tumors may also activate angiogenic inhibitors such as angiostatin (U.S. Pat. No. 5,639,725, herein incorporated by reference) and endostatin that can modulate angiogenesis both at the primary site and at downstream sites of metastasis. The potential use of these and other natural and synthetic angiogenic inhibitors as anticancer drugs is currently under intense investigation (see, e.g. Zetter, 1998, Ann. Rev. Med. 49:407–427). Such agents may have reduced toxicity and be less likely to generate drug resistance than conventional cytotoxic drugs. Clinical trials are now underway to develop optimum treatment strategies for antiangiogenic agents.

Angiopoietin-1 (Ang-1) is an angiogenic factor that signals through the endothelial cell-specific Tie2 receptor tyrosine kinase. Like VEGF, Ang- I is essential for normal endothelial developmental processes in the mouse (Davis et al., 1996, Cell 87:). Furthermore, Ang-1 induces the formation of capillary sprouts (Koblizek et al., 1998, Curr. Biol. 8:529–532). The protein is expressed only on endothelial cells and early hemopoietic cells (e.g., see Sure et al., 1996, Cell 87:1171–1180).

Angiopoietin-2 (Ang-2) is a naturally occurring antagonist for Ang1 and Tie2 and can disrupt blood vessel formation in the mouse embryos (see, eg. Maisonpierre et al., 1997, Science 277:55-). Ang-2 is expressed only at sites of vascular remodeling.

In animal models some angiogenesis-dependent diseases can be controlled via induction or inhibition of new vessel formation. Treatment of diseases by modulation of angiogenesis are currently tested in clinical trials. Thus the manipulation of new vessel formation in angiogenesis-dependent conditions such as wound healing, inflammatory diseases, ischemic heart and peripheral vascular disease, myocardial infarction, diabetic retinopathy, and cancer is likely to create new therapeutic options.

Thus, angiogenesis is believed to play a significant role in the metastasis of a cancer and in the ischemic heart and ischemic vascular disease. If this angiogenic activity could be repressed or eliminated, then the tumor, although present, would not grow. In the disease state, prevention of angiogenesis could avert the damage caused by the invasion of the new microvascular system. If this angiogenic activity could be stimulated or induced, ischemic tissues in the heart and brain and mycocardial necrosis could be prevented. In the disease state, stimulation or induction of angiogenesis could avert the damage. Therapies directed at control of the angiogenic processes could lead to the abrogation or mitigation of these diseases.

Novel angiogenic and antiangiogenic molecules are needed, both to model unwanted growth of blood vessels, especially into tumors, and for therapies directed to preventing such unwanted growth. In certain antiangiogenic embodiments, the compositions and methods of this invention are useful in inhibiting the activity of endogenous growth factors in premetastatic tumors and preventing the formation of the capillaries in the tumors thereby inhibiting the growth of the tumors. The composition, and antibodies specific to the composition, should also be able to modulate the formation of capillaries in other angiogenic processes, such as wound healing and reproduction. Finally, the composition and method for inhibiting angiogenesis should preferably be non-toxic and produce few side effects.

SUMMARY OF THE INVENTION

The present invention is directed to novel molecules, referred to herein as "angiopoeitin-3 (Ang-3)", "human microvascular endothelial differentiation gene 1 (hMEDG1)" and "heart specific growth factor-8b (FGF-8b)" polypeptides, as well as nucleic acid sequences encoding those molecules.

In certain preferred embodiments, the novel nucleic acid sequences of this invention is operatively linked to one or more expression control sequences. The invention also provides a host cell, including bacterial, plant, yeast, insect and mammalian cells, that produce the novel polypeptides, whether the cell is transformed with the nucleic acid sequences encoding those proteins, or whether the cell is transformed with regulatory sequences to activate or enhance production of these proteins from an endogenous nucleic acid sequence encoding same.

Processes are also provided for producing a protein, which comprise growing a culture of host cells producing such proteins (as described above) in a suitable culture medium, and purifying the protein from the culture. The protein produced according to such methods is also provided by the present invention. In preferred embodiments the protein comprises an angiopoeitin-3, hMEDG1 and FGF-8b amino acid sequence or fragments thereof, the protein being substantially free from other mammalian proteins. Such compositions may further comprise a pharmaceutically acceptable carrier. Compositions comprising an antibody which specifically reacts with such protein are also contemplated by the present invention. Methods are also contemplated for preventing, treating or ameliorating a medical condition which comprises administering to a mammalian subject a therapeutically effective amount of a composition comprising a protein of the present invention and a pharmaceutically acceptable carrier.

In certain angiogenic embodiments, the compositions and methods of this invention are useful in stimulating the growth of blood vessels, especially in mycocardial infarction and other heart diseases or brain infarcts (strokes). The composition should be able to overcome the necrotic effects of ischemic tissue and thereby prevent the effects of heart diseases or strokes. Finally, the composition and method for stimulating angiogenesis should preferably be non-toxic and produce few side effects.

The proteins disclosed in this invention are likely to play a role in angiogenesis. Accordingly, the compositions and methods of this invention are useful in anti-cancer and heart disease therapies. Diagnostic, prognostic and screening kits are also contemplated.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a representation of the nucleotide sequence (SEQ ID NO:1) and deduced amino acid sequence (SEQ ID NO:2) of an angiopoeitin-3 (Ang-3). The signal sequence is underlined.

FIG. 2 is a representation of the nucleotide sequence (SEQ ID NO:3) and deduced amino acid sequence (SEQ ID NO:4) of hMEDG1. The signal sequence is underlined.

FIGS. 3A and 3B are a representation of the nucleotide sequence (SEQ ID NO:5) and deduced amino acid sequence (SEQ ID NO:6) of heart specific growth factor 8b (FGF-8b). Panel A shows the preliminarily determined sequence, with the signal sequence underlined. Panel B shows the confirmed sequence.

DETAILED DESCRIPTION OF THE INVENTION

Figure 4:
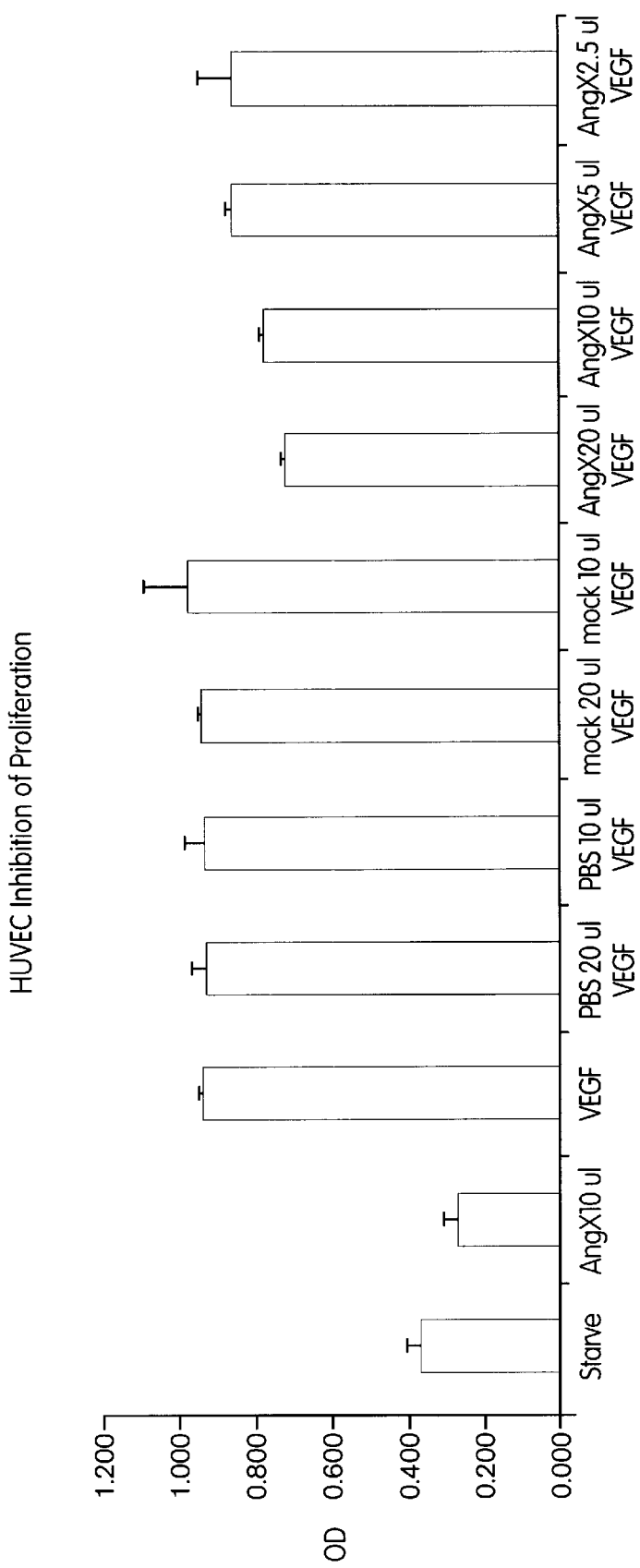
FIG. 4 is a histogram showing the effects of various agents on the proliferation of human vascular endothelial endothelial cells (HUVEC).

The invention provides for novel angiopoeitin-3, hMEDG1, or FGF-8b proteins and genes encoding those proteins, as well as derivatives, homologs, active fragments and analogs, from various species, particularly vertebrates, and more particularly mammals. In some embodiments, the polypeptides modulate angiogenic/antiangiogenic activites. As used herein, the term "direct angiogenic/antiangiogenic molecules" means a molecule that elicits an effect on angiogenesis/antiangiogenesis in vivo upon exogenous administration or overexpression, that has an effect on relevant endothelial cells in vitro that is compatible with angiogenesis/antiangiogenesis, and the role of the molecule has been established in a process or disease.

In a preferred embodiment, the foregoing proteins and genes are of human origin. Production of the foregoing proteins and derivatives, e.g, by recombinant methods, is also contemplated in the present invention. In other specific embodiments, the fragment, derivative or analog is functionally active, i.e., capable of exhibiting one or more functional activity associated with wild type Ang3, hMEDG1, or FGF-8b protein. Such functional activities include, but are not limited to, the stimulation or inhibition of angiogenesis and related disorders and the treatment of heart disease and related disorders. Such functional activities include further, but are not limited to, antigenicity or ability to bind (or compete with Ang-3, hMEDG1, or FGF-8b for binding) to an anti-Ang3, anti-hMEDG1, or anti-FGF-8b antibody, respectively], immunogenicity (ability to generate an antibody that binds to anti-IP-Ang3, anti-IP-hMEDG1, or anti-IP-heart specific growth factor, respectively), etc.

The invention provides novel Ang-X nucleic acid sequences. A novel Ang-X nucleic acid includes the polynucleotide sequence set forth in FIG. 1. The nucleotide sequence includes a coding region extending from nucleotides 352 to 1824. This polynucleotide has been named "Angiopoeitin-3 (Ang-3)". The amino acid sequence of the protein encoded by Ang-3 is also shown in FIG. 1. Ang-3 was isolated from a human heart library, cloned into a vector and sequenced by methods known in the art.

To isolate a Ang-3 nucleic acid, messenger RNA (mRNA) was purified from total cellular RNA isolated from various human organs which were commercially-available from Clontech (e.g., Fetal brain, heart, kidney, fetal liver, liver, lung, skeletal muscle, pancreas and placenta) utilizing an Oligotex™ cDNA synthesis kit (QIAGEN, Inc.; Chatsworth, Calif.). The first-strand of the cDNA was prepared from 1.0 $\mu$g of poly(A)$^+$ RNA with 200 pmols of oligo(dT)25V (wherein V=A, C or G) using 400 units of Superscript II reverse transcriptase (BRL; Grand Island N.Y.). Following the addition of 10 units of E. coli DNA ligase, 40 units of E. coli DNA polymerase, and 3.5 units of E. coli RNase H (all supplied by BRL; Grand Island, N.Y.), second-strand synthesis was performed at 16° C. for 2 hours. Five units of T$_4$ DNA polymerase was then added, and incubation was continued for an additional 5 minutes at 16° C. The reaction was then treated with 5 units of arctic shrimp alkaline phosphatase (U.S. Biochemicals; Cleveland Ohio) at 37° C. for 30 minutes, and the cDNA was purified by standard phenol/chloroform (50:50 v/v) extraction. The yield of cDNA was estimated using fluorometry with the Picogreen™ Labeling System (Molecular Probes; Eugene, Oreg.).

Following synthesis, the double-stranded cDNA was digested with various restriction enzymes, ligated to linkers compatible with the over-hanging termini generated by the restriction digestion. The restriction fragments were amplified utilizing 30 cycles of polymerase chain reaction (PCR) by the addition of the following reagents: 2 $\mu$l 10 mM dNTP; 5 $\mu$l 10×TB buffer (500 mM Tris, 160 mM $(NH4)_2SO_4$; 20 mM $MgCl_2$, pH 9.15); 0.25 $\mu$l Klentaq (Clontech Advantage): PFU (Stratagene; La Jolla Calif.) in a 16:1 v/v ratio; 32.75 $\mu$l ddH2O. The amplification products were then ligated into the TA™ cloning vector (Invitrogen). Individual clones were subjected to dye-primer, double-stranded DNA sequencing utilizing PCR products which were derived from amplification using vector-specific primers, which flanked the insertion, site as templates. Sequencing was performed using a standard chemistry methdology on ABI Model 377 sequencers (Molecular Dynamics).

The nucleic acid sequence in FIG. 1 encodes a novel protein, Ang-3. Sequence homology algorithms, e.g., BLASTN/BLASTX or FASTA searches, revealed no exact sequence matches. A BLASTX search revealed 59% homology between Ang-3 (in the approximate region of nucleotides 1067 and 1833 of FIG. 1), and human angiopoietin proteins (including human Ang1 [GenBank Accession Number U83508] and human Ang-2 [GenBank Accession Number AF004327]. A BLASTP search also revealed 63% homology between Ang-3 (in the approximate region of amino acids 269 to 491 of FIG. 1), and human angiopoietin proteins (including human angiopoetin-like protein (CDT6 gene) [GenBank Accession Number Y16132]). Furthermore, a BLASTP search revealed 51% homology between Ang-3 (in the approximate region of amino acids 8 to 491 of FIG. 1), and mouse angiopoietin-1 protein [GenBank Accession Number U83509]). Finally, a BLASTP search revealed 61% homology between Ang-3 (in the approximate region of amino acids 277 to 491 of FIG. 1) and fibrinogen-like proteins (including fibrinogen-like protein 1 precursor [TREMBL Accession Number Q08830]), fibrinogen-related protein HFREP-1 precursor [PIR Accession Number JN0596] and fibrinogen-like protein [TREMBL Accession Number Q143114]).

Analysis of the full-length Ang-3 sequence revealed that this clone contains a signal sequence. Related polypeptides also include signal sequences. For example, Ang-2 is known to have a secretion signal peptide. Ang-1 and Ang-2 are 60% identical. Furthermore, Ang-3 is homologous in the carboxy-terminal fibrinogen-like domain to Ang-1 and Ang-2 (Maisonpierre et al., 1997, Science 277:55–60). Based upon these homologies, Ang-3 and these homologous likely share at least some activities.

In one embodiment, the present invention provides an isolated polynucleotide selected from the group consisting of:

(a) a polynucleotide comprising the nucleotide sequence shown in FIG. 1 from nucleotide 352 to nucleotide 1824, or nucleotide 415 to nucleotide 1824;

(b) a polynucleotide comprising a fragment of the nucleotide sequence shown in FIG. 1 encoding a protein having biological activity;

(c) a polynucleotide encoding a protein comprising the amino acid sequence shown in FIG. 1, from nucleotide 352 to nucleotide 1824 (i.e., including the signal sequence) or from nucleotide 415 to nucleotide 1824 (the mature peptide), herein called angiopoetin-3;

(d) a polynucleotide encoding a protein comprising a fragment of the amino acid sequence shown in FIG. 1 having biological activity;

(e) a polynucleotide capable of hybridizing under stringent conditions to any one of the polynucleotides specified in (a)–(d).

The sequence of a polynucleotide encoding another protein of the present invention is set forth in FIG. 2. The coding region extends from nucleotides 190 to 858. This polynucleotide has been named "Microvascular Endothelial Differentiation Gene" (hMEDG1). The amino acid sequence of the protein encoded by the endothelial differentiation gene (hMEDG1) is set forth in FIG. 2. HMEDG1 was isolated from a human heart library, cloned into a vector and sequenced by methods known in the art.

The nucleic acid sequence in FIG. 2 encodes a novel protein, hMEDG1. Sequence homology algorithms, e.g., BLASTN/BLASTX or FASTA searches revealed no exact sequence matches. A BLASTX search revealed 84% homology between the hMEDG1 protein (in the approximate region of nucleotides 56–1013 of FIG. 2 and rat microvascular endothelial differentiation gene 1 (GenBank Accession Number X98993). BLASTP search revealed 94% homology between the hMEDG1 protein (in the approximate region of amino acids 51–223 of FIG. 2) and rat microvascular endothelial differentiation gene 1 (SPTREMBL-Acc. No. 97554). Analysis of the protein sequences revealed that the N-terminus of hMEDG1 contains 50 amino acids that were not reported in the rat MEDG1 protein. These 50 amino acids comprise a signal sequence; therefore hMEDG1 does encode a secreted factor. Based upon these homologies, hMEDG1 and these homologous proteins are expected to share at least some activities.

Accordingly, in this embodiment, the present invention provides a composition comprising an isolated polynucleotide selected from the group consisting of:

(a) a polynucleotide comprising the nucleotide sequence shown in FIG. 2 from nucleotide 51 to nucleotide 858, or from nucleotide 259 to nucleotide 858;

(b) a polynucleotide comprising a fragment of the nucleotide sequence shown in FIG. 2 encoding a protein having biological activity;

(c) a polynucleotide encoding a protein comprising the amino acid sequence shown in FIG. 2, from nucleotide 51 to nucleotide 858 (i.e., including the signal sequence) or nucleotide 259 to nucleotide 858 (the mature peptide), herein called human microvascular endothelial differention gene 1;

(d) a polynucleotide encoding a protein comprising a fragment of the amino acid sequence shown in FIG. 2 having biological activity;

(e) a polynucleotide capable of hybridizing under stringent conditions to any one of the polynucleotides specified in (a)–(d).

The sequence of a polynucleotide encoding another protein of the present invention is set forth in FIG. 3, with the coding region extending from nucleotides 39 to 618 (Panel A) and 39 to 659 (Panel B). This polynucleotide has been identified as "human heart specific fibroblast growth factor 8b (FGF-8b)" The amino acid sequence of the protein encoded by FGF-8b is set forth in FIG. 3. The human FGF-8b was isolated from a human heart library using a trap which selects for nucleotides encoding secreted proteins; therefore, FGF-8b encodes a secreted factor.

The nucleic acid sequence in FIG. 3 encodes a novel protein, FGF-8b. Panel A shows a preliminarily determined sequence. Panel B shows a confirmed sequence. We prefer the sequence in Panel B. Sequence homology algorithms, e.g., BLASTN/BLASTX or FASTA searches revealed no exact sequence matches. A BLASTP search revealed about 80% homology between the FGF-8b (particularly in the approximate region of amino acids 1–181 of FIG. 3) and various human growth factors including fibroblast growth factor 8, androgen-induced growth factor, keratinocyte growth factor, heparin-binding growth factor-1, and beta-endothelial cell growth factor (including without limitation those assigned accession numbers G2660747, P55075, P36363, P10935, E68414). BLASTX searches confirmed these results. Based upon these homologies, FGF-8b and these homologous proteins are expected to share at least some activities.

In another embodiment, the present invention provides a composition comprising an isolated polynucleotide selected from the group consisting of:

(a) a polynucleotide comprising the nucleotide sequence shown in FIG. 3 from nucleotide 39 to nucleotide 618, or from nucleotide 120 to nucleotide 618;

(b) a polynucleotide comprising a fragment of the nucleotide sequence shown in FIG. 3 encoding a protein having biological activity;

(c) a polynucleotide encoding a protein comprising the amino acid sequence shown in FIG. 3, from nucleotide 39 to nucleotide 618 (i.e., including the signal sequence) or nucleotide 120 to nucleotide 618 (the mature peptide), herein called heart specific growth factor 8b as initially determined;

(d) a polynucleotide encoding a protein comprising a fragment of the amino acid sequence shown in FIG. 3 having biological activity;

(e) a polynucleotide capable of hybridizing under stringent conditions to any one of the polynucleotides specified in (a)–(d).

In a further embodiment, the present invention provides a composition comprising an isolated polynucleotide selected from the group consisting of:

(a) a polynucleotide comprising the nucleotide sequence shown in FIG. 3B from nucleotide 39 to nucleotide 659, or from nucleotide 120 to nucleotide 618;

(b) a polynucleotide comprising a fragment of the nucleotide sequence shown in FIG. 3 encoding a protein having biological activity;

(c) a polynucleotide encoding a protein comprising the amino acid sequence shown in FIG. 3, from nucleotide 39 to nucleotide 659 (i.e., including the signal sequence) or nucleotide 120 to nucleotide 659 (the mature peptide), herein called heart specific growth factor 8b;

(d) a polynucleotide encoding a protein comprising a fragment of the amino acid sequence shown in FIG. 3 having biological activity;

(e) a polynucleotide capable of hybridizing under stringent conditions to any one of the polynucleotides specified in (a)–(d).

The tissue distribution of Ang-3, hMEDG1 and FGF-8b is shown in Table 1:

TABLE I

|  | Heart | Lung | Brain | Kidney | Testis | Liver | Muscle | Pancreas | Bone |
|---|---|---|---|---|---|---|---|---|---|
| Ang-3 | +++ | +++ | ++ | ++ | ++ | ++ | ++ | ++ | – |
| hMEDG1 | + | – | – | – | – | – | – | – | – |
| FGF-8b | +++ | ++ | + | – | – | – | + | – | – |

++ = strong expression
++ = moderate expression
+ = weak expression
– = expression not detected Nucleic acids encoding Ang3, hMEDG1, or FGF-8b can be obtained by any method known in the art, e.g, by PCR amplification using synthetic primers that hybridize to the 3' and 5' ends of the sequence and/or by cloning from a cDNA or genomic library using an oligonucleotide specific for the gene sequence, e.g., as described infra.

Homologs, e.g., of nucleic acids encoding Ang3, hMEDG1, or FGF-8b of species other than human, or other related sequences, e.g., paralogs, can be obtained by low, moderate or high stringency hybridization with all or a portion of the particular human sequence as a probe using methods well known in the art for nucleic acid hybridization and cloning, e.g., as described infra, for Ang3, hMEDG1, or FGF-8b nucleotide sequences.

Polynucleotides hybridizing to the polynucleotides of the present invention under stringent conditions and highly stringent conditions are also part of the present invention. As used herein, "highly stringent conditions" include, for example, at least about 0.2 times SSC at 65 degree C; and "stringent conditions" include, for example, hybridization in 50% formamide, 1 M NaCl, 1% SDS at 37 C, and a wash in 0.1×SSC (20×SSC=3.0 M NaCl/0.3 M trisodium citrate) at 60–65 C. Preferred high stringency conditions are hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65 C, and a wash in 0.1×SSC, 0.1% SDS at 65 C. Allelic variants of the polynucleotides of the present invention are also encompassed by the invention.

Expression of Recombinant Proteins

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 ells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, the protein can be produced in lower eukaryotes such as yeast, or in prokaryotes such as bacteria. Yeast strains can include, e.g., *Saccharomyces cerevisiae, Schizosaccharomyces pombe*, Kluyveromyces strains, Candida spp., or any other yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac.R™. kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

Biological Activity of Protein Fragments

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

Protein Purification

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl R™, or Cibacrom blue 3GA Sepharose R™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

Modified Proteins

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584, incorporated by reference).

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides of the present invention and the proteins encoded thereby are expected to exhibit one or more of the uses or biological activities identified below. Uses or activities described for proteins of the present invention may be provided by administration or use of such proteins or by administration or use of polynucleotides encoding such proteins (such as, for example, in gene therapies or vectors suitable for introduction of DNA).

The biological activity of the proteins of this invention can be assayed by any suitable method known in the art. The angiogenic/antiangiogenic potential can be characterized in angiogenesis assays in vivo such as the chick chorionic allantoic membrane (CAM) assay or different cornea micropocket assays (Klagsbrun & Folkman, 1990, In: Sporn & Roberts (eds). Peptide growth factors and their receptors II, pp. 549–574). An a in vivo angiogenesis assay is described in, eg., U.S. Pat. No. 5,382,514, incorporated by reference), and a mouse model of hindlimb ischemia was described by Couffinhal et al., 1998, Am. J. Pathol. 152:1667–1679). Direct effects of angiogenic molecules on vascular wall cells can be assayed in in vitro assays. These assays facilitate the study of endothelial functions that are essential for new blood vessel formation. Most in vitro models of angiogenesis use extracellular matrix substrata containing growth-regulatory molecules (Vukicevic et al., 1992, Exp. Cell. Res. 202:1–8). Furthermore, most assays cell culture assay for angiopoietin to test the formation of capillary sprouts (see, eg. Koblizek et al., 1998, Curr. Biol. 8:529–532). Most assays require exogenous stimuli such as phorbol esters or angiogenic molecules to induce the formation of endothelial cords and tubes. Assays for angiogenic/antiangiogenic activity include methods for inhibition of angiogenesis (see, for example, but not limited to, U.S. Pat. Nos. 5,733,876, 5,639,725, 5,712,291, 5,698,586, 5,753,230, 5,733,876, 5,766,591, 5,434,185, 5,721,226, 5,629,340 5,593,990, 5,629,327, 5,744,492, 5,646,136, 5,610,166, 5,574,026, 5,567,693, 5,563,130, each herein fully incorporated by reference).

Angiogenic Stimulation/Inhibition Activity

A protein of the present invention may exhibit angiogenic (either inducing or inhibiting) or cell differentiation (either inducing or inhibiting) activity. Many protein factors discovered to date, including all known angiopoeitins and growth factors, have exhibited activity in one or more factor dependent cell proliferation assays, and hence the assays serve as a convenient confirmation of angiogenic activity. The activity of a protein of the present invention is evidenced by any one of a number of routine factor dependent cell proliferation assays for cell lines including, without limitation, 32D, DA2, DA1G, T10,B9, B9/11, BaF3, MC9/G, M+(preB M+), 2E8, RB5, DA1,123, T1165, HT2, CTLL2, TF-1, Mo7e and CMK.

Methods of diagnosis, prognosis, and screening for diseases and disorders associated with aberrant levels of an Ang3, hMEDG1, or heart specific growth factor, are contemplated. The invention also contemplates methods of treating or preventing diseases or disorders associated with aberrant levels of an Ang3, hMEDG1, or heart specific growth factor, or aberrant levels of activity of one or more of the components of the complex, comprising administration of the Ang3, hMEDG1, or heart specific growth factor.

Methods of assaying an Ang3, hMEDG1, or FGF-8b, for activity as therapeutics or diagnostics as well as methods of screening modulators (i.e., inhibitors, agonists and antagonists) are also contemplated.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular Ang3, hMEDG1, or FGF-8b to minimize side effects of the Ang3, hMEDG1, or FGF-8b agent.

Administration of protein of the present invention used in the pharmaceutical composition or to practice the method of the present invention can be carried out in a variety of conventional ways, such as oral ingestion, inhalation, or cutaneous, subcutaneous, or intravenous injection. When a therapeutically effective amount of protein of the present invention is administered by intravenous, cutaneous or subcutaneous injection, protein of the present invention will be in the form of a pyrogen-free, parenterally-acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

A protein of the present invention may be active in multimers (e.g., heterodimers or homodimers) or complexes with itself or other proteins. As a result, pharmaceutical compositions of the invention may comprise a protein of the invention in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing Ang3, hMEDG1, or heart specific growth factor. When co-administered with one or more Ang3, hMEDG 1, or FGF-8b, protein of the present invention may be administered either simultaneously with the Ang3, HMEDG1, or FGF-8b, or sequentially. If administered sequentially, the attending physician will decide on the appropriate sequence of administering protein of the present invention in combination with Ang3, hMEDG1, or FGF-8b.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further.

Accordingly, in one aspect, the invention includes a method for inhibiting cell proliferation by providing a cell (e.g., ex vivo, in vitro, or in vivo) in an amount sufficient to inhibit proliferation of the cell. The cell can be, e.g., en endothelial cell such as a human vascular endothelial cell. The Ang-3 polypeptide can include, e.g, an amino acid sequence of a polypeptide encoded by nucleotide 425 to nucleotide 1824 of FIG. 1 (SEQ ID NO:2), e.g., nucleotide 352 to nucleotide 1824 of FIG. 1 (SEQ ID NO:2).

The invention also provides a method for inhibiting the growth of a tumor in a subject by administering to the subject an Ang-3 polypeptide in an amount sufficient to inhibit the growth of the tumor. The Ang-3 polypeptide can include, e.g., the amino acid sequence of a polypeptide encoded by nucleotide 425 to nucleotide 1824 of FIG. 1 (SEQ ID NO:2).

The subject is preferably a mammal, e.g., a human, or non-human primate, dog, cat, horse, cow, or pig.

Also within the invention is a method for inhibiting the growth of a tumor in a subject by administering to the subject an amount of an Ang-3 nucleic acid in an amount sufficient to inhibit the growth of the tumor. The nucleic acid preferably includes, the amino acid encoded by nucleotide 352 to nucleotide 1824 of FIG. 1 (SEQ ID NO:2),e.g., the amino acid sequence of a polypeptide encoded by nucleotide 425 to nucleotide 1824 of FIG. 1.

Also within the invention is a method for inhibiting tumor metastasis in a subject by administering to the subject an amount of an Ang-3 polypeptide in an amount sufficient to inhibit metastasis of the tumor. Alternatively, a nucleic acid encoding an Ang-3 polypeptide can be administered in an amount sufficient to inhibit metastasis of the tumor. The tumor can be, e.g., a fibrosarcoma or a carcinoma. The metastasis that is inhibited can be, e.g., a lung metastasis.

Antibodies

A protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

Gene Therapy

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

The invention will be further illustrated in the following examples, which do not limit the scope of the claims.

EXAMPLE 1

Ang-3 Inhibits Proliferation of HUVEC Cells

The effect o Ang-3 on proliferation of human umbilical vein endothelial cell (HUVEC) was examined. The results of three trials are presented in FIGS. 4–6.

Partially conditioned medium, as indicated, was added to HUVEC cells. After 18 hours, BrdU was added to the cells. After five hours of incubation, BrdU incorporation was detected using ELISA.

The results of one attempt are shown in FIG. 4. Proliferation was measured by measuring change in cell number by measuring OD. Proliferation was measured in cells treated as indicated in FIG. 4.

Addition of Ang-3 to HUVEC cells resulted in fewer cells (compare "AngX 10 $\mu$l to "Starve").

The effect of Ang-3 was also examined in cells exposed to vascular endothelial growth factor ("VEGF"). First, the effect of VEGF on HUVEC cell number was measured. FIG. 4 also shows that addition of VEGF resulted in increased number HUVEC cells as compared to starved cells (compare "VEGF" to "Starve").

Next, the effect of PBS or culture supernatant from cells transformed with a control expression vector on the proliferative effect of VEGF was measured. Addition of 20 $\mu$l of PBS along with VEGF or addition of 10 $\mu$l of PBS along with VEGF did not significantly change the HUVEC cell number compared to administration of VEGF alone. Addition of 20 $\mu$l of mock conditioned medium along with VEGF, or 10 $\mu$l of mock conditioned medium along with VEGF, also did not significantly change the HUVEC cell number compared to administration of VEGF alone.

Administration of Ang-3 along with VEGF resulted in significantly fewer cells as compared to administration of VEGF alone. FIG. 4 shows that the Ang-3 mediated inhibition is dose-dependent. Greatest inhibition was observed when 20 $\mu$l of Ang-3 is added along with VEGF, while less inhibition was detected when 10 $\mu$l, 5 $\mu$l, or 2.5 $\mu$l of Ang-3 was added.

Figure 5:
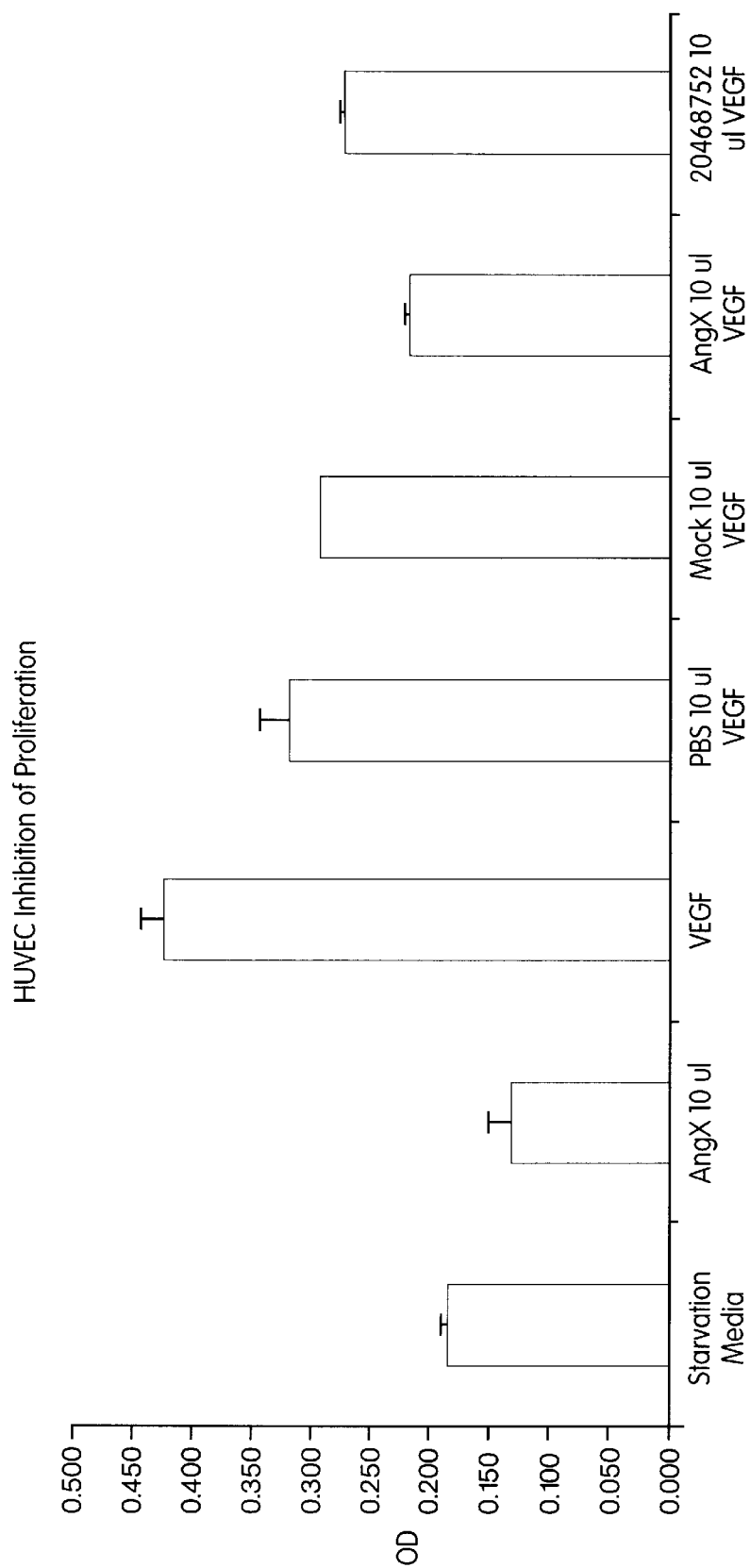
FIG. 5 is a histogram showing the effects of various agents on the proliferation of human vascular endothelial endothelial cells (HUVEC).
Figure 6:
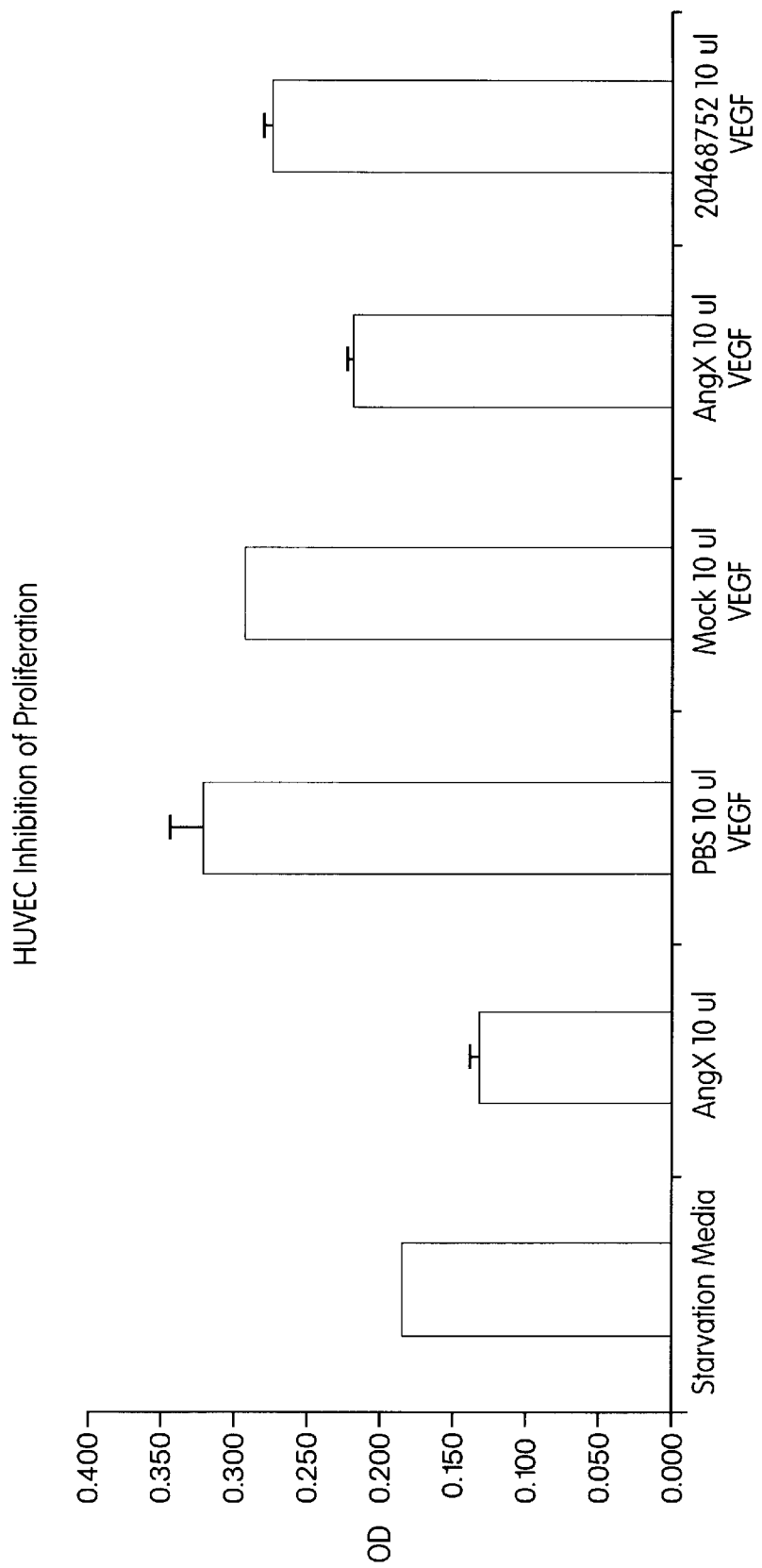
FIG. 6 is a histogram showing the effects of various agents on the proliferation of human vascular endothelial endothelial cells (HUVEC).

A second and third demonstration of the effect of Ang-3 on proliferation of HUVEC cells is shown in FIG. 5 and FIG. 6. Significantly fewer cells were observed in Ang-3 treated cells as compared to cells exposed to starvation media. In contrast, administration of VEGF in the presence of 10 $\mu$l of PBS or 10 $\mu$l of mock medium resulted in significantly higher HUVEC cell numbers. Addition of AngX inhibited the proliferative effects of VEGF. Cell number was not significantly different in cells exposed to VEGF and mock medium and cells exposed to VEGF and a control protein named "20468752". The 2046875 protein is disclosed in PCT/US00/21857, filed Aug. 11, 2000, and has 565 residues (99%) identical to, and positive with a 720 residue human protein designated PRO1344 (see, PCT Publication WO 9963088-A2), and has 51 of 150 residues (34%) identical to, and 71 of 150 residues (47%) positive with the 699 residue human complement-activating component of RA-reactive factor precursor (EC 3.4.21.-) (RA-reactive factor serine protease P100) (RARF) (mannose-binding protein associated serine protease) (MASP) (ACC:P48740).

These results demonstrate that Ang-3 protein inhibits proliferation of human cells in vitro. The data also demonstrate that this inhibition occurs when cells are exposed to the growth factor VEGF.

EXAMPLE 2

Ang-3 Inhibits Metastasis of Lung Carcinomas

Figure 7A:
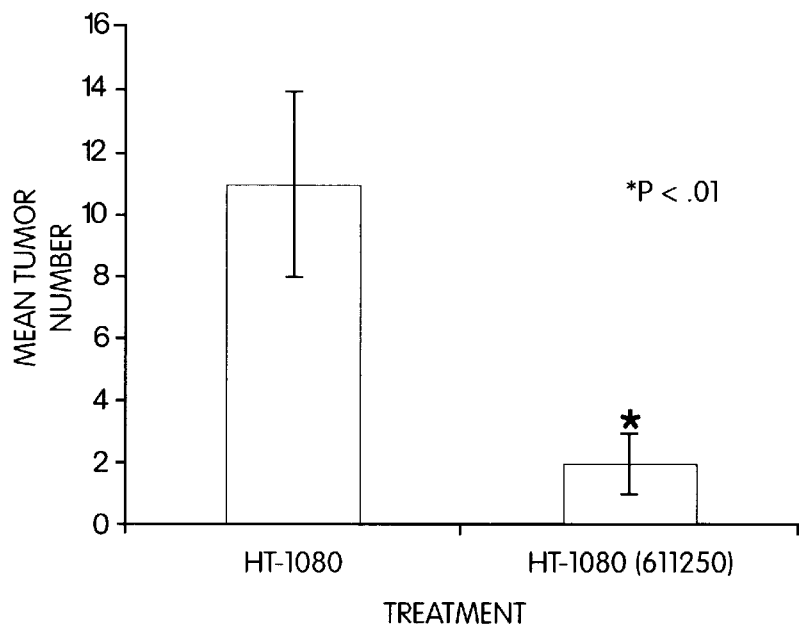
FIGS. 7A and 7B are histograms showing the effect of Ang-3 on lung metastasis of a HT-1080 fibrosacroma.
Figure 7B:
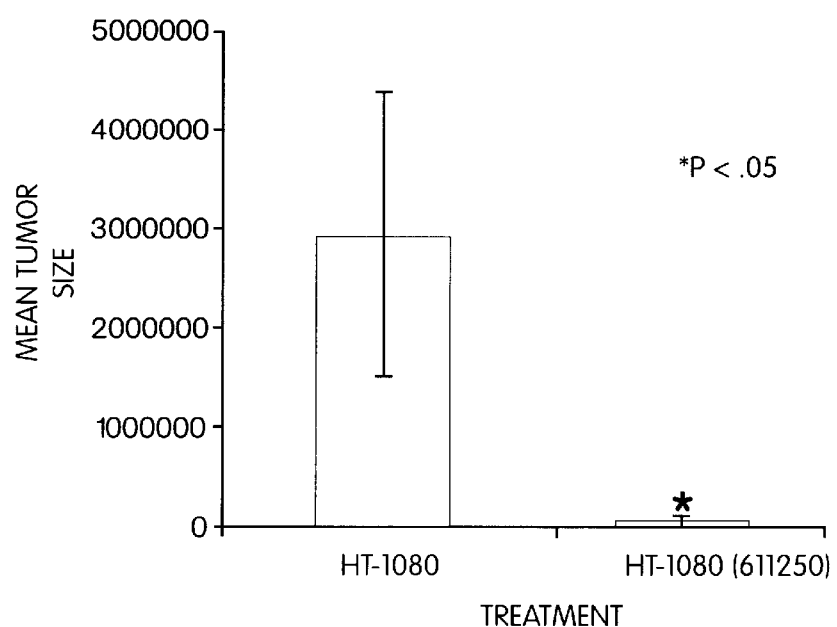

The effect of Ang-3 on metastasis of lung carcinomas in the human HT-1080 fibrosarcoma system was examined. HT-1080 cells were implanted in host animals. Animals were then sacrificed and their lungs examined for tumor number and tumor size. The results are shown in FIG. 7A and 7B. Animals exposed to Ang-3 (denoted "611250") t had significantly fewer tumor numbers and had a significantly smaller tumor size. These results show that the Ang-3 polypeptide can inhibit metastases of fibrosarcoma.

We claim:

1. A method for inhibiting cell proliferation, the method comprising providing a cell; and contacting said cell with a mature Ang-3 polypeptide shown in FIG. 1 (amino acids 22–491 of SEQ ID NO:2) in an amount sufficient to inhibit proliferation of said cell.

2. The method of claim 1, wherein said cell is provided in vitro, ex vivo, or in vivo.

3. The method of claim 1, wherein said cell is an endothelial cell.

4. A method for inhibiting cell proliferation, the method comprising providing a cell; and contacting said cell with an Ang-3 protein shown in FIG. 1 (amino acids 1–491 of SEQ ID NO:2) in an amount sufficient to inhibit proliferation of said cell.

* * * * *

SEQUENCE LISTING

<160> NUMBER OF SEQ ID NOS: 8

<210> SEQ ID NO 1
<211> LENGTH: 2354
<212> TYPE: DNA
<213> ORGANISM: Homo sapiens
<220> FEATURE:
<221> NAME/KEY: CDS
<222> LOCATION: (352)..(1824)

<400> SEQUENCE: 1

```
atctgggtca gctgcagctg gttactgcat ttctccatgt ggcagacaga gcaaagccac    60
aacgctttct ctgctggatt aaagacggcc cacagaccag aacttccact atactactta   120
aaattacata ggtggcttgt caaattcaat tgattagtat tgtaaaagga aaaagaagtt   180
ccttcttaca gcttggattc aacggtccaa aacaaaaatg cagctgccat taaagtcaca   240
gatgaacaaa cttctacact gattttaaa atcaagaata agggcagcaa gtttctggat    300
tcactgaatc aacagacaca aaaagacatc attttacaac ctcatttcaa a atg aag   357
                                                           Met Lys
                                                             1 act ttt acc tgg acc cta ggt gtg cta ttc ttc cta cta gtg gac act    405
Thr Phe Thr Trp Thr Leu Gly Val Leu Phe Phe Leu Leu Val Asp Thr
        5                   10                  15 gga cat tgc aga ggt gga caa ttc aaa att aaa aaa ata aac cag aga    453
Gly His Cys Arg Gly Gly Gln Phe Lys Ile Lys Lys Ile Asn Gln Arg
 20                  25                  30 aga tac cct cgt gcc aca gat ggt aaa gag gaa gca aag aaa tgt gca    501
Arg Tyr Pro Arg Ala Thr Asp Gly Lys Glu Glu Ala Lys Lys Cys Ala
 35                  40                  45                  50 tac aca ttc ctg gta cct gac caa aga ata aca ggg cca atc tgt gtc    549
Tyr Thr Phe Leu Val Pro Asp Gln Arg Ile Thr Gly Pro Ile Cys Val
                 55                  60                  65 aac acc aag ggg caa gat gca agt acc att aaa gac atg atc acc agg    597
Asn Thr Lys Gly Gln Asp Ala Ser Thr Ile Lys Asp Met Ile Thr Arg
             70                  75                  80 atg gac ctt gaa aac ctg aag gat gtg ctc tcc agg cag aag cgg gag    645
Met Asp Leu Glu Asn Leu Lys Asp Val Leu Ser Arg Gln Lys Arg Glu
         85                  90                  95 ata gat gtt ctg caa ctg gtg gtg gat gta gat gga aac att gtg aat    693
Ile Asp Val Leu Gln Leu Val Val Asp Val Asp Gly Asn Ile Val Asn
    100                 105                 110 gag gta aag ctg ctg aga aag gaa agc cgt aac atg aac tct cgt gtt    741
Glu Val Lys Leu Leu Arg Lys Glu Ser Arg Asn Met Asn Ser Arg Val
115                 120                 125                 130 act caa ctc tat atg caa tta tta cat gag att atc cgt aag agg gat    789
Thr Gln Leu Tyr Met Gln Leu Leu His Glu Ile Ile Arg Lys Arg Asp
                135                 140                 145 aat tca ctt gaa ctt tcc caa ctg gaa aac aaa atc ctc aat gtc acc    837
Asn Ser Leu Glu Leu Ser Gln Leu Glu Asn Lys Ile Leu Asn Val Thr
            150                 155                 160 aca gaa atg ttg aag atg gca aca aga tac agg gaa cta gag gtg aaa    885
Thr Glu Met Leu Lys Met Ala Thr Arg Tyr Arg Glu Leu Glu Val Lys
        165                 170                 175 tac gct tcc ttg act gat ctt gtc aat aac caa tct gtg atg atc act    933
Tyr Ala Ser Leu Thr Asp Leu Val Asn Asn Gln Ser Val Met Ile Thr
    180                 185                 190 ttg ttg gaa gaa cag tgc ttg agg ata ttt tcc cga caa gac acc cat    981
Leu Leu Glu Glu Gln Cys Leu Arg Ile Phe Ser Arg Gln Asp Thr His
```

-continued

```
                195                 200                 205                 210
gtg tct ccc cca ctt gtc cag gtg gtg cca caa cat att cct aac agc         1029
Val Ser Pro Pro Leu Val Gln Val Val Pro Gln His Ile Pro Asn Ser
                215                 220                 225 caa cag tat act cct ggt ctg ctg gga ggt aac gag att cag agg gat         1077
Gln Gln Tyr Thr Pro Gly Leu Leu Gly Gly Asn Glu Ile Gln Arg Asp
                230                 235                 240 cca ggt tat ccc aga gat tta atg cca cca cct gat ctg gca act tct         1125
Pro Gly Tyr Pro Arg Asp Leu Met Pro Pro Pro Asp Leu Ala Thr Ser
                245                 250                 255 ccc acc aaa agc cct ttc aag ata cca ccg gta act ttc atc aat gaa         1173
Pro Thr Lys Ser Pro Phe Lys Ile Pro Pro Val Thr Phe Ile Asn Glu
                260                 265                 270 gga cca ttc aaa gac tgt cag caa gca aaa gaa gct ggg cat tcg gtc         1221
Gly Pro Phe Lys Asp Cys Gln Gln Ala Lys Glu Ala Gly His Ser Val
275                 280                 285                 290 agt ggg att tat atg att aaa cct gaa aac agc aat gga cca atg cag         1269
Ser Gly Ile Tyr Met Ile Lys Pro Glu Asn Ser Asn Gly Pro Met Gln
                295                 300                 305 tta tgg tgt gaa aac agt ttg gac cct ggg ggt tgg act gtt att cag         1317
Leu Trp Cys Glu Asn Ser Leu Asp Pro Gly Gly Trp Thr Val Ile Gln
                310                 315                 320 aaa aga aca gac ggc tct gtc aac ttc ttc aga aat tgg gaa aat tat         1365
Lys Arg Thr Asp Gly Ser Val Asn Phe Phe Arg Asn Trp Glu Asn Tyr
                325                 330                 335 aag aaa ggg ttt gga aac att gac gga gaa tac tgg ctt gga ctg gaa         1413
Lys Lys Gly Phe Gly Asn Ile Asp Gly Glu Tyr Trp Leu Gly Leu Glu
                340                 345                 350 aat atc tat atg ctt agc aat caa gat aat tac aag tta ttg att gaa         1461
Asn Ile Tyr Met Leu Ser Asn Gln Asp Asn Tyr Lys Leu Leu Ile Glu
355                 360                 365                 370 tta gaa gac tgg agt gat aaa aaa gtc tat gca gaa tac agc agc ttt         1509
Leu Glu Asp Trp Ser Asp Lys Lys Val Tyr Ala Glu Tyr Ser Ser Phe
                375                 380                 385 cgt ctg gaa cct gaa agt gaa ttc tat aga ctg cgc ctg gga act tac         1557
Arg Leu Glu Pro Glu Ser Glu Phe Tyr Arg Leu Arg Leu Gly Thr Tyr
                390                 395                 400 cag gga aat gca ggg gat tct atg atg tgg cat aat ggt aaa caa ttc         1605
Gln Gly Asn Ala Gly Asp Ser Met Met Trp His Asn Gly Lys Gln Phe
                405                 410                 415 acc aca ctg gac aga gat aaa gat atg tat gca gga aac tgc gcc cac         1653
Thr Thr Leu Asp Arg Asp Lys Asp Met Tyr Ala Gly Asn Cys Ala His
                420                 425                 430 ttt cat aaa gga ggc tgg tgg tac aat gcc tgt gca cat tct agc cta         1701
Phe His Lys Gly Gly Trp Trp Tyr Asn Ala Cys Ala His Ser Ser Leu
435                 440                 445                 450 aat gga gta tgg tac aga gga ggc cat tac aga agc aag cac caa gat         1749
Asn Gly Val Trp Tyr Arg Gly Gly His Tyr Arg Ser Lys His Gln Asp
                455                 460                 465 gga att ttc tgg gcc gaa tac aga ggc ggg tca tac tcc tta aga gca         1797
Gly Ile Phe Trp Ala Glu Tyr Arg Gly Gly Ser Tyr Ser Leu Arg Ala
                470                 475                 480 gtt cag atg atg atc aag cct att gac tgaagagaga cactcgccaa              1844
Val Gln Met Met Ile Lys Pro Ile Asp
                485                 490 tttaaatgac acagaacttt gtacttttca gctcttaaaa atgtaaatgt tacatgtata      1904
ttacttggca caatttattt ctacacataa agttttttaaa atgaatttta ccgtaactat     1964
aaaagggaac ctataaatgt agtttcatct gtcgtcaatt actgcagaaa attatgtgta     2024
```

```
tccacaacct agttatttta aaaattatgt tgactaaata caaagtttgg tttctaaaat    2084
gtaaatattt gccacaatgt aaagcaaatc ttagctatat tttaaatcat aaataacatg    2144
ttcaagatac ttaacaattt atttaaaatc taagattgct ctaacgtcta gtgaaaaaaa    2204
tatttttaaa atttcagcca aatgatgcat tttatttata aaaatacaga cagaaaatta    2264
gggagaaacc tctagttttg ccaatagaaa atgcttcttc cattgaataa aagttatttc    2324
aaatccaaaa aaaaaaaaaa aaaaaaaaa                                      2354
```

<210> SEQ ID NO 2
<211> LENGTH: 491
<212> TYPE: PRT
<213> ORGANISM: Homo sapiens

<400> SEQUENCE: 2

```
Met Lys Thr Phe Thr Trp Thr Leu Gly Val Leu Phe Phe Leu Leu Val
 1               5                  10                  15

Asp Thr Gly His Cys Arg Gly Gly Gln Phe Lys Ile Lys Lys Ile Asn
             20                  25                  30

Gln Arg Arg Tyr Pro Arg Ala Thr Asp Gly Lys Glu Glu Ala Lys Lys
         35                  40                  45

Cys Ala Tyr Thr Phe Leu Val Pro Asp Gln Arg Ile Thr Gly Pro Ile
     50                  55                  60

Cys Val Asn Thr Lys Gly Gln Asp Ala Ser Thr Ile Lys Asp Met Ile
 65                  70                  75                  80

Thr Arg Met Asp Leu Glu Asn Leu Lys Asp Val Leu Ser Arg Gln Lys
                 85                  90                  95

Arg Glu Ile Asp Val Leu Gln Leu Val Val Asp Val Asp Gly Asn Ile
            100                 105                 110

Val Asn Glu Val Lys Leu Leu Arg Lys Glu Ser Arg Asn Met Asn Ser
        115                 120                 125

Arg Val Thr Gln Leu Tyr Met Gln Leu Leu His Glu Ile Ile Arg Lys
    130                 135                 140

Arg Asp Asn Ser Leu Glu Leu Ser Gln Leu Glu Asn Lys Ile Leu Asn
145                 150                 155                 160

Val Thr Thr Glu Met Leu Lys Met Ala Thr Arg Tyr Arg Glu Leu Glu
                165                 170                 175

Val Lys Tyr Ala Ser Leu Thr Asp Leu Val Asn Asn Gln Ser Val Met
            180                 185                 190

Ile Thr Leu Leu Glu Glu Gln Cys Leu Arg Ile Phe Ser Arg Gln Asp
        195                 200                 205

Thr His Val Ser Pro Pro Leu Val Gln Val Val Pro Gln His Ile Pro
    210                 215                 220

Asn Ser Gln Gln Tyr Thr Pro Gly Leu Leu Gly Gly Asn Glu Ile Gln
225                 230                 235                 240

Arg Asp Pro Gly Tyr Pro Arg Asp Leu Met Pro Pro Asp Leu Ala
                245                 250                 255

Thr Ser Pro Thr Lys Ser Pro Phe Lys Ile Pro Pro Val Thr Phe Ile
            260                 265                 270

Asn Glu Gly Pro Phe Lys Asp Cys Gln Gln Ala Lys Glu Ala Gly His
        275                 280                 285

Ser Val Ser Gly Ile Tyr Met Ile Lys Pro Glu Asn Ser Asn Gly Pro
    290                 295                 300

Met Gln Leu Trp Cys Glu Asn Ser Leu Asp Pro Gly Gly Trp Thr Val
```

```
305                 310                 315                 320
Ile Gln Lys Arg Thr Asp Gly Ser Val Asn Phe Phe Arg Asn Trp Glu
                325                 330                 335

Asn Tyr Lys Lys Gly Phe Gly Asn Ile Asp Gly Glu Tyr Trp Leu Gly
            340                 345                 350

Leu Glu Asn Ile Tyr Met Leu Ser Asn Gln Asp Asn Tyr Lys Leu Leu
        355                 360                 365

Ile Glu Leu Glu Asp Trp Ser Asp Lys Lys Val Tyr Ala Glu Tyr Ser
    370                 375                 380

Ser Phe Arg Leu Glu Pro Glu Ser Glu Phe Tyr Arg Leu Arg Leu Gly
385                 390                 395                 400

Thr Tyr Gln Gly Asn Ala Gly Asp Ser Met Met Trp His Asn Gly Lys
                405                 410                 415

Gln Phe Thr Thr Leu Asp Arg Asp Lys Asp Met Tyr Ala Gly Asn Cys
            420                 425                 430

Ala His Phe His Lys Gly Gly Trp Trp Tyr Asn Ala Cys Ala His Ser
        435                 440                 445

Ser Leu Asn Gly Val Trp Tyr Arg Gly Gly His Tyr Arg Ser Lys His
    450                 455                 460

Gln Asp Gly Ile Phe Trp Ala Glu Tyr Arg Gly Gly Ser Tyr Ser Leu
465                 470                 475                 480

Arg Ala Val Gln Met Met Ile Lys Pro Ile Asp
                485                 490
```

<210> SEQ ID NO 3
<211> LENGTH: 1014
<212> TYPE: DNA
<213> ORGANISM: Homo sapiens
<220> FEATURE:
<221> NAME/KEY: CDS
<222> LOCATION: (190)..(858)

<400> SEQUENCE: 3

```
cgcccgggca gtgcccgggg aaggaggagc gctaggtcgg tgtacgaccg agattagggt      60
gcgtgccagc tccgggaggc cgcggtgagg ggccgggccc aagctgccga cccgagccga     120
tcgtcagggt cgccagcgcc tcagctctgt ggaggagcag cagtagtcgg agggtgcagg     180 atattagaa atg gct act ccc cag tca att ttc atc ttt gca atc tgc att     231
         Met Ala Thr Pro Gln Ser Ile Phe Ile Phe Ala Ile Cys Ile
           1               5                  10 tta atg ata aca gaa tta att ctg gcc tca aaa agc tac tat gat atc      279
Leu Met Ile Thr Glu Leu Ile Leu Ala Ser Lys Ser Tyr Tyr Asp Ile
 15                  20                  25                  30 tta ggt gtg cca aaa tcg gca tca gag cgc caa atc aag aag gcc ttt      327
Leu Gly Val Pro Lys Ser Ala Ser Glu Arg Gln Ile Lys Lys Ala Phe
                 35                  40                  45 cac aag ttg gcc atg aag tac cac cct gac aaa aat aag agc ccg gat      375
His Lys Leu Ala Met Lys Tyr His Pro Asp Lys Asn Lys Ser Pro Asp
             50                  55                  60 gct gaa gca aaa ttc aga gag att gca gaa gca tat gaa aca ctc tca      423
Ala Glu Ala Lys Phe Arg Glu Ile Ala Glu Ala Tyr Glu Thr Leu Ser
         65                  70                  75 gat gct aat aga cga aaa gag tat gat aca ctt gga cac agt gct ttt      471
Asp Ala Asn Arg Arg Lys Glu Tyr Asp Thr Leu Gly His Ser Ala Phe
     80                  85                  90 act agt ggt aaa gga caa aga ggt agt gga agt tct ttt gag cag tca      519
Thr Ser Gly Lys Gly Gln Arg Gly Ser Gly Ser Ser Phe Glu Gln Ser
 95                 100                 105                 110
```

```
ttt aac ttc aat ttt gat gac tta ttt aaa gac ttt ggc ttt ttt ggt     567
Phe Asn Phe Asn Phe Asp Asp Leu Phe Lys Asp Phe Gly Phe Phe Gly
                115                 120                 125 caa aac caa aac act gga tcc aag aag cgt ttt gaa aat cat ttc cag     615
Gln Asn Gln Asn Thr Gly Ser Lys Lys Arg Phe Glu Asn His Phe Gln
            130                 135                 140 aca cgc cag gat ggt ggt tcc agt aga caa agg cat cat ttc caa gaa     663
Thr Arg Gln Asp Gly Gly Ser Ser Arg Gln Arg His His Phe Gln Glu
                145                 150                 155 ttt tct ttt gga ggt gga tta ttt gat gac atg ttt gaa gat atg gag     711
Phe Ser Phe Gly Gly Gly Leu Phe Asp Asp Met Phe Glu Asp Met Glu
        160                 165                 170 aaa atg ttt tct ttt agt ggt ttt gac tct acc aat cag cat aca gta     759
Lys Met Phe Ser Phe Ser Gly Phe Asp Ser Thr Asn Gln His Thr Val
175                 180                 185                 190 cag act gaa aat aga ttt cat gga tct agc aag cac tgc agg act gtc     807
Gln Thr Glu Asn Arg Phe His Gly Ser Ser Lys His Cys Arg Thr Val
                195                 200                 205 act caa cga aga gga aat atg gtt act aca tac act gac tgt tca gga     855
Thr Gln Arg Arg Gly Asn Met Val Thr Thr Tyr Thr Asp Cys Ser Gly
            210                 215                 220 cag tagttcttat tctattctca ctaaatccaa ctggttgact cttcctcatt          908
Gln atctttgatg ctaaacaatt ttctgtgaac tattttgaca agtgcatgat ttcactttaa   968
acaatttgat atagctatta aatatattta agggtttttt tttttg                  1014

<210> SEQ ID NO 4
<211> LENGTH: 223
<212> TYPE: PRT
<213> ORGANISM: Homo sapiens

<400> SEQUENCE: 4

Met Ala Thr Pro Gln Ser Ile Phe Ile Phe Ala Ile Cys Ile Leu Met
  1               5                  10                  15

Ile Thr Glu Leu Ile Leu Ala Ser Lys Ser Tyr Tyr Asp Ile Leu Gly
             20                  25                  30

Val Pro Lys Ser Ala Ser Glu Arg Gln Ile Lys Lys Ala Phe His Lys
         35                  40                  45

Leu Ala Met Lys Tyr His Pro Asp Lys Asn Lys Ser Pro Asp Ala Glu
     50                  55                  60

Ala Lys Phe Arg Glu Ile Ala Glu Ala Tyr Glu Thr Leu Ser Asp Ala
 65                  70                  75                  80

Asn Arg Arg Lys Glu Tyr Asp Thr Leu Gly His Ser Ala Phe Thr Ser
                 85                  90                  95

Gly Lys Gly Gln Arg Gly Ser Gly Ser Ser Phe Glu Gln Ser Phe Asn
            100                 105                 110

Phe Asn Phe Asp Asp Leu Phe Lys Asp Phe Gly Phe Phe Gly Gln Asn
        115                 120                 125

Gln Asn Thr Gly Ser Lys Lys Arg Phe Glu Asn His Phe Gln Thr Arg
    130                 135                 140

Gln Asp Gly Gly Ser Ser Arg Gln Arg His His Phe Gln Glu Phe Ser
145                 150                 155                 160

Phe Gly Gly Gly Leu Phe Asp Asp Met Phe Glu Asp Met Glu Lys Met
                165                 170                 175

Phe Ser Phe Ser Gly Phe Asp Ser Thr Asn Gln His Thr Val Gln Thr
            180                 185                 190
```

```
Glu Asn Arg Phe His Gly Ser Ser Lys His Cys Arg Thr Val Thr Gln
        195                 200                 205
Arg Arg Gly Asn Met Val Thr Thr Tyr Thr Asp Cys Ser Gly Gln
    210                 215                 220

<210> SEQ ID NO 5
<211> LENGTH: 688
<212> TYPE: DNA
<213> ORGANISM: Homo sapiens
<220> FEATURE:
<221> NAME/KEY: CDS
<222> LOCATION: (39)..(617)
<221> NAME/KEY: misc_feature
<222> LOCATION: (619)
<223> OTHER INFORMATION: Wherein n is a or t or c or g.

<400> SEQUENCE: 5
ggctgggcta ggagccgccg cctccctccc gcccagcg atg tat tca gcg ccc tcc        56
                                          Met Tyr Ser Ala Pro Ser
                                            1               5 gcc tgc act tgc ctg tgt tta cac ttc ctg ctg ctg tgc ttc cag gta        104
Ala Cys Thr Cys Leu Cys Leu His Phe Leu Leu Leu Cys Phe Gln Val
         10                  15                  20 cag gtg ctg gtt gcc gag gag aac gtg gac ttc cgc atc cac gtg gag        152
Gln Val Leu Val Ala Glu Glu Asn Val Asp Phe Arg Ile His Val Glu
     25                  30                  35 aac cag acg cgg gct cgg gac gat gtg agc cgt aag cag ctg cgg ctg        200
Asn Gln Thr Arg Ala Arg Asp Asp Val Ser Arg Lys Gln Leu Arg Leu
 40                  45                  50 tac cag ctc tac agc cgg acc agt ggg aaa cac atc cag gtc ctg ggc        248
Tyr Gln Leu Tyr Ser Arg Thr Ser Gly Lys His Ile Gln Val Leu Gly
 55                  60                  65                  70 cgc agg atc agt gcc cgc ggc gag gat ggg gac aag tat gcc cag ctc        296
Arg Arg Ile Ser Ala Arg Gly Glu Asp Gly Asp Lys Tyr Ala Gln Leu
                 75                  80                  85 cta gtg gag aca gac acc ttc ggt agt caa gtc cgg atc aag ggc aag        344
Leu Val Glu Thr Asp Thr Phe Gly Ser Gln Val Arg Ile Lys Gly Lys
         90                  95                 100 gag acg gaa ttc tac ctg tgc atg aac cgc aaa ggc aag ctc gtg ggg        392
Glu Thr Glu Phe Tyr Leu Cys Met Asn Arg Lys Gly Lys Leu Val Gly
     105                 110                 115 aag ccc gat ggc acc agc aag gag tgt gtg ttc atc gag aag gtt ctg        440
Lys Pro Asp Gly Thr Ser Lys Glu Cys Val Phe Ile Glu Lys Val Leu
 120                 125                 130 gag aac aac tac acg gcc ctg atg tcg gct aag tac tcc ggc tgg tac        488
Glu Asn Asn Tyr Thr Ala Leu Met Ser Ala Lys Tyr Ser Gly Trp Tyr
135                 140                 145                 150 gtg ggc ttt acc aag aag ggg cgg ccg cgg aag ggc ccc aag acc cgg        536
Val Gly Phe Thr Lys Lys Gly Arg Pro Arg Lys Gly Pro Lys Thr Arg
                155                 160                 165 gag aac cag cag gac gtg cat ttc att gaa gcg cta ccc caa ggg gca        584
Glu Asn Gln Gln Asp Val His Phe Ile Glu Ala Leu Pro Gln Gly Ala
            170                 175                 180 acc cgg agc ttt aga agc cct tca agt aca cga cngtgaccaa gaagtcccgt     637
Thr Arg Ser Phe Arg Ser Pro Ser Ser Thr Arg
        185                 190 ccggatccgg cccacacacc ctgcctaagg gcaacccgcc gcggggcccc t               688

<210> SEQ ID NO 6
<211> LENGTH: 193
<212> TYPE: PRT
```

<213> ORGANISM: Homo sapiens

<400> SEQUENCE: 6

```
Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
             20                  25                  30

Phe Arg Ile His Val Glu Asn Gln Thr Arg Ala Arg Asp Asp Val Ser
         35                  40                  45

Arg Lys Gln Leu Arg Leu Tyr Gln Leu Tyr Ser Arg Thr Ser Gly Lys
     50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Ile Glu
                165                 170                 175

Ala Leu Pro Gln Gly Ala Thr Arg Ser Phe Arg Ser Pro Ser Ser Thr
            180                 185                 190

Arg
```

<210> SEQ ID NO 7
<211> LENGTH: 833
<212> TYPE: DNA
<213> ORGANISM: Homo sapiens
<220> FEATURE:
<221> NAME/KEY: CDS
<222> LOCATION: (39)..(659)
<221> NAME/KEY: misc_feature
<222> LOCATION: (771)
<223> OTHER INFORMATION: Wherein n is a or t or c or g.
<221> NAME/KEY: misc_feature
<222> LOCATION: (778)
<223> OTHER INFORMATION: Wherein n is a or t or c or g.

<400> SEQUENCE: 7

```
ggctgggcta ggagccgccg cctccctccc gcccagcg atg tat tca gcg ccc tcc      56
                                         Met Tyr Ser Ala Pro Ser
                                          1               5 gcc tgc act tgc ctg tgt tta cac ttc ctg ctg ctg tgc ttc cag gta       104
Ala Cys Thr Cys Leu Cys Leu His Phe Leu Leu Leu Cys Phe Gln Val
            10                  15                  20 cag gtg ctg gtt gcc gag gag aac gtg gac ttc cgc atc cac gtg gag       152
Gln Val Leu Val Ala Glu Glu Asn Val Asp Phe Arg Ile His Val Glu
        25                  30                  35 aac cag acg cgg gct cgg gac gat gtg agc cgt aag cag ctg cgg ctg       200
Asn Gln Thr Arg Ala Arg Asp Asp Val Ser Arg Lys Gln Leu Arg Leu
    40                  45                  50 tac cag ctc tac agc cgg acc agt ggg aaa cac atc cag gtc ctg ggc       248
Tyr Gln Leu Tyr Ser Arg Thr Ser Gly Lys His Ile Gln Val Leu Gly
55                  60                  65                  70
```

-continued

```
cgc agg atc agt gcc cgc ggc gag gat ggg gac aag tat gcc cag ctc    296
Arg Arg Ile Ser Ala Arg Gly Glu Asp Gly Asp Lys Tyr Ala Gln Leu
             75                  80                  85 cta gtg gag aca gac acc ttc ggt agt caa gtc cgg atc aag ggc aag    344
Leu Val Glu Thr Asp Thr Phe Gly Ser Gln Val Arg Ile Lys Gly Lys
         90                  95                 100 gag acg gaa ttc tac ctg tgc atg aac cgc aaa ggc aag ctc gtg ggg    392
Glu Thr Glu Phe Tyr Leu Cys Met Asn Arg Lys Gly Lys Leu Val Gly
        105                 110                 115 aag ccc gat ggc acc agc aag gag tgt gtg ttc atc gag aag gtt ctg    440
Lys Pro Asp Gly Thr Ser Lys Glu Cys Val Phe Ile Glu Lys Val Leu
    120                 125                 130 gag aac aac tac acg gcc ctg atg tcg gct aag tac tcc ggc tgg tac    488
Glu Asn Asn Tyr Thr Ala Leu Met Ser Ala Lys Tyr Ser Gly Trp Tyr
135                 140                 145                 150 gtg ggc ttc acc aag aag ggg cgg ccg cgg aag ggc ccc aag acc cgg    536
Val Gly Phe Thr Lys Lys Gly Arg Pro Arg Lys Gly Pro Lys Thr Arg
                155                 160                 165 gag aac cag cag gac gtg cat ttc atg aag cgc tac ccc aag ggg cag    584
Glu Asn Gln Gln Asp Val His Phe Met Lys Arg Tyr Pro Lys Gly Gln
            170                 175                 180 ccg gag ctt cag aag ccc ttc aag tac acg acg gtg acc aag agg tcc    632
Pro Glu Leu Gln Lys Pro Phe Lys Tyr Thr Thr Val Thr Lys Arg Ser
        185                 190                 195 cgt cgg atc cgg ccc aca cac cct gcc taggccaccc cgccgcggcc         679
Arg Arg Ile Arg Pro Thr His Pro Ala
    200                 205 cctcaggtcg ccctggccac actcacactc ccagaaaact gcatcagagg aatattttta  739
catgaaaaat aaggaagaag ctctattttt gncattgng tttaaaagaa gacaaaaact   799
gaaccaaaac tcttgggggg agggtgata agga                               833

<210> SEQ ID NO 8
<211> LENGTH: 207
<212> TYPE: PRT
<213> ORGANISM: Homo sapiens

<400> SEQUENCE: 8

Met Tyr Ser Ala Pro Ser Ala Cys Thr Cys Leu Cys Leu His Phe Leu
  1               5                  10                  15

Leu Leu Cys Phe Gln Val Gln Val Leu Val Ala Glu Glu Asn Val Asp
                 20                  25                  30

Phe Arg Ile His Val Glu Asn Gln Thr Arg Ala Arg Asp Asp Val Ser
             35                  40                  45

Arg Lys Gln Leu Arg Leu Tyr Gln Leu Tyr Ser Arg Thr Ser Gly Lys
         50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160
```

-continued

```
Lys Gly Pro Lys Thr Arg Glu Asn Gln Gln Asp Val His Phe Met Lys
            165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
            195                 200                 205
```